US008833175B2

(12) United States Patent
Chandrasekharan et al.

(10) Patent No.: US 8,833,175 B2
(45) Date of Patent: Sep. 16, 2014

(54) STRUCTURE AND FABRICATION OF A MICROSCALE FLOW-RATE/SKIN FRICTION SENSOR

(75) Inventors: Vijay Chandrasekharan, Gainesville, FL (US); Jeremy Sells, Gainesville, FL (US); Mark Sheplak, Gainesville, FL (US); David P. Arnold, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 587 days.

(21) Appl. No.: 13/133,303

(22) PCT Filed: Mar. 13, 2009

(86) PCT No.: PCT/US2009/037158
§ 371 (c)(1),
(2), (4) Date: Jun. 7, 2011

(87) PCT Pub. No.: WO2010/104518
PCT Pub. Date: Sep. 16, 2010

(65) Prior Publication Data
US 2011/0314924 A1 Dec. 29, 2011

(51) Int. Cl.
*G01L 1/00* (2006.01)
*G01B 7/16* (2006.01)
(52) U.S. Cl.
USPC .............................................. 73/780; 29/847
(58) Field of Classification Search
USPC ......................................................... 73/780
See application file for complete search history.

(56) References Cited

U.S. PATENT DOCUMENTS

| 6,966,231 B2 * | 11/2005 | Sheplak et al. ................. 73/861 |
| 2005/0092106 A1 * | 5/2005 | Sheplak et al. .......... 73/862.623 |
| 2006/0137467 A1 * | 6/2006 | Horowitz et al. ............... 73/815 |
| 2011/0032512 A1 * | 2/2011 | Horowitz et al. ............ 356/35.5 |

OTHER PUBLICATIONS

Desai and Haque, "Design and fabrication of a direction sensitive MEMS shear stress sensor with high spatial and temporal resolution," Journal of Micromechanics and Microengineering, 2004, vol. 14, pp. 1718-1725.
Hyman et al., "Microfabricated Shear Stress Sensors, Part 2: Testing and Calibration," AIAA Journal, 1999, vol. 37, No. 1, pp. 73-78.
Li et al., "Tolerance analysis for comb-drive actuator using DRIE fabrication," Sensors and Actuators A 12, 2006, pp. 494-503.
Loeppert and Bee, "SiSonic—The First Commercialized MEMS Microphone," Solid-State Sensors, Actuators, and Microsystems Workshop, Hilton Head Island, South Carolina, Jun. 4-8, 2006, pp. 27-30.

(Continued)

*Primary Examiner* — Lisa Caputo
*Assistant Examiner* — Jamel Williams
(74) *Attorney, Agent, or Firm* — Saliwanchik, Lloyd & Eisenschenk

(57) ABSTRACT

A floating element shear sensor and method for fabricating the same are provided. According to an embodiment, a microelectromechanical systems (MEMS)-based capacitive floating element shear stress sensor is provided that can achieve time-resolved turbulence measurement. In one embodiment, a differential capacitive transduction scheme is used for shear stress measurement. The floating element structure for the differential capacitive transduction scheme incorporates interdigitated comb fingers forming differential capacitors, which provide electrical output proportional to the floating element deflection.

26 Claims, 22 Drawing Sheets

(56) References Cited

OTHER PUBLICATIONS

O'Grady et al., "A MEMS Sensor for Mean Shear Stress Measurements in High-Speed Turbulent Flows with Backside Interconnects," Transducers 2009, Denver, CO, Jun. 2009, pp. 272-275.

Pan et al., "Characterization of Microfabricated Shear Stress Sensors," In: Proc. International Conference on Solid-State Sensors and Actuators and Eurosensors IX, Stockholm, Sweden, 1995, pp. 443-446.

Pan et al., "Microfabricated Shear Stress Sensors, Part 1: Design and Fabrication," AIAA Journal, Jan. 1999, vol. 37, No. 1, pp. 66-72.

Schmidt et al., "Design and Calibration of a Microfabricated Floating-Element Shear-Stress Sensor," IEEE Transaction of Electrical Devices, Jun. 1988, vol. 35, No. 6, pp. 750-757.

Sheplak et al., "MEMS Shear Stress Sensors: Promise and Progress," In: Proc. $24^{th}$ AIAA Aerodynamic Measurement Technology and Ground Testing Conference, Portland, OR, Jun. 2004, pp. 1-13.

Soundararajan et al., "MEMS Shear Stress Sensors for Microcirculation," Sensor and Actuators A 118, 2004, pp. 25-32.

Tiliakos et al., "A MEMS-based Shear Stress Sensor for High Temperature Applications," $46^{th}$ Annual Aerospace Sciences Meeting and Exhibit, Reno, NV, Jan. 2008, pp. 1-9.

Tiliakos et al., "MEMS Shear Stress Sensor for Hypersonic Aeropropulsion Test and Evaluation," 2006 Annual ITEA Technology Review, pp. 1-15.

Zhe et al., "A Microfabricated Wall Shear-Stress Sensor with Capacitive Sensing," Journal of Microelectromechanical Systems, Feb. 2005, vol. 14, No. 1, pp. 167-175.

\* cited by examiner

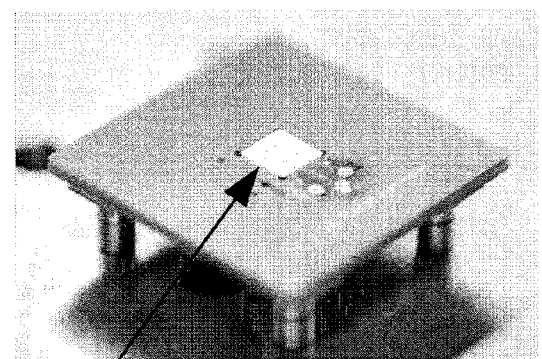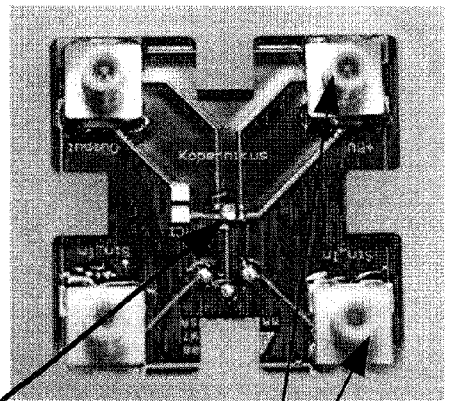
FIG. 32A — Flush mounted sensor
FIG. 32B — SiSonic™ voltage follower; SMB connectors
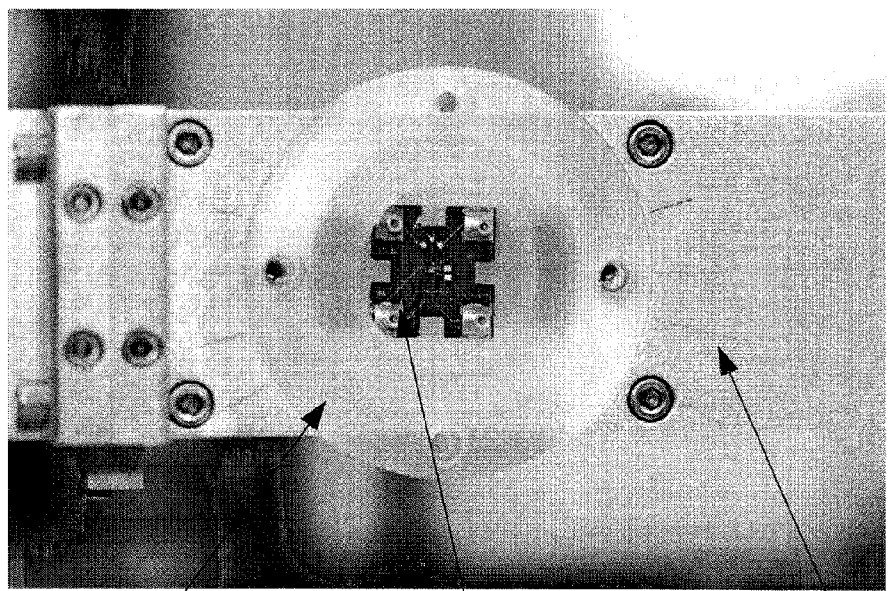
FIG. 33 — Lucite Plug; Sensor PCB; Plane Wave Tube (PWT)

STRUCTURE AND FABRICATION OF A MICROSCALE FLOW-RATE/SKIN FRICTION SENSOR

GOVERNMENT SUPPORT

This invention was made with government support under award number NNX07AB27A awarded by NASA. The government has certain rights in the invention.

CROSS REFERENCE TO RELATED APPLICATION

This application is the U.S. national stage application of International Application Serial No. PCT/US2009/037158, filed Mar. 13, 2009, which is hereby incorporated by reference in its entirety, including all figures, tables and drawings.

BACKGROUND OF THE INVENTION

The measurement of time-resolved wall shear stress is an important aspect for both fundamental scientific studies and applied aerodynamic applications. In general, wall shear stress is the friction between a moving fluid and adjacent surface. Wall shear can also be referred to as skin friction, which can be used to determine drag, transition, and flow separation. In engine applications, wall shear stress can lower efficiency and increase fuel consumption. In particular, quantitative measurement of wall shear stress has received considerable attention in development of aerospace vehicles. Applications for wall shear stress measurement include feedback sensors for flow control. However, despite several research efforts, time-accurate, continuous, direct measurement of fluctuating shear stress has been elusive due to stringent spatial and temporal resolution requirements.

Currently, MEMS sensors exist for both direct and indirect shear stress measurement. Indirect sensors rely on a correlation between a measured flow property and the shear stress. Previously reported micromachined indirect shear stress sensors include thermal sensors, micro-fences, micro-pillars, and laser based sensors. In contrast, direct sensors measure the integrated shear force on a sensing area such as a floating-element structure. Micromachined direct sensors in the past have used capacitive, optical, and piezoresistive, transduction schemes. Each sensor design demonstrated progress towards the development of shear stress sensors. However, the prior sensors have shown limited performance in terms of sensitivity drift, and insufficient dynamic range, bandwidth, and/or minimum detectable signal (MDS).

BRIEF SUMMARY OF THE INVENTION

Embodiments of the present invention relate to direct wall shear stress measurement. Implementations of the present invention can be applicable to sensor applications including but not limited to capacitive sensors, flow rate sensors, shear stress sensors, and accelerometers. Certain embodiments can be applicable to comb drive actuators.

According to an embodiment, the subject sensor can utilize a differential capacitive transduction scheme. Implementations of the subject sensor can address one or more performance parameters, dynamic range, bandwidth and minimum detectable signal (MDS) issues.

In an embodiment utilizing the differential capacitive transduction scheme, dissimilar/asymmetric comb fingers can be incorporated on a floating element structure for in-plane motion measurement.

In a further embodiment, damping and cavity compliance can be used to minimize out-of-plane sensitivity, which can be achieved by moving the cut-on frequency of out-of-plane signal beyond the desired bandwidth for in-plane motion. The cavity stiffness may also be used for minimizing out of plane sensitivity, as it lowers the overall out-of-plane compliance.

According to an embodiment, sensitivity of the subject sensor can be improved by incorporating additional capacitance between tethers, the floating element and the substrate.

According to an embodiment, a method for fabricating the subject sensor can include front and back side etching of a substrate. The substrate can be a semiconductor substrate and/or a substrate having a conductive device layer backed by an electrically insulating handle layer. In a specific embodiment using a silicon-on insulator (SOI) substrate, a silicon dioxide ($SiO_2$) wet etch can be performed for sensor fabrication.

The dissimilar/asymmetric comb fingers of sensor embodiments can be fabricated using bulk micromachining or surface micromachining in a single mask process. In addition, the micromachining can be used to achieve flush mounting of sensor for flow measurements. Backside cavity and damping incorporated in embodiments of the subject sensor can effectively lower out-of-plane sensitivity.

In one embodiment, metal can be directly electroplated onto a conductive silicon/semiconductor substrate to form the electrostatic device. For example, the metal can be directly electroplated on a doped silicon substrate. In a specific embodiment, the metal can be Nickel. In another embodiment, metal can be electroplated on a SOI substrate with a highly doped (conductive) top layer and a high resistivity (non-conductive) bottom layer. By utilizing the highly doped top layer, metal can be selectively plated on only the capacitive structure of the subject sensor and not on the bulk silicon underneath.

According to an embodiment, the subject sensor can include metal passivation for the microfabricated electrostatic sensors/actuators to inhibit drift due to charge accumulation (due to humidity/moisture) on the surface. The metal passivation can be formed through any suitable metal deposition technique, including but not limited to electroplating, sputtering, evaporation electroless plating, and chemical vapor deposition.

Embodiments of the present invention can be fabricated using a two mask fabrication process. The two mask fabrication process can significantly lower fabrication cost and time, improving efficiency.

BRIEF DESCRIPTION OF THE DRAWINGS

FIG. 2A shows a top view and FIG. 2B shows a side view along section. A-A of FIG. 2A.

FIG. 30A relates to pressure sensitivity and cavity compliance; and FIG. 30B provides an equivalent circuit for the differential capacitive shear stress sensor according to an embodiment of the present invention.

FIGS. 32A and 32B show photographs of a sensor packaged on a (30 mm×30 mm) PCB board and inserted into a lucite plug according to an embodiment of the present invention. FIG. 32A shows a top-side perspective view and FIG. 32B shows a bottom view.

FIG. 33 shows an image of a packaged sensor mounted on a plane wave tube (PWT) for dynamic shear stress measurements.

DETAILED DISCLOSURE OF THE INVENTION

Embodiments of the present invention provide a flow-rate/skin friction/shear stress sensor. In one embodiment, the shear stress sensor can be a MEMS-based floating element shear stress sensor. In a further embodiment, the floating element shear stress sensor can utilize a differential capacitive transduction scheme.

Figure 1A:
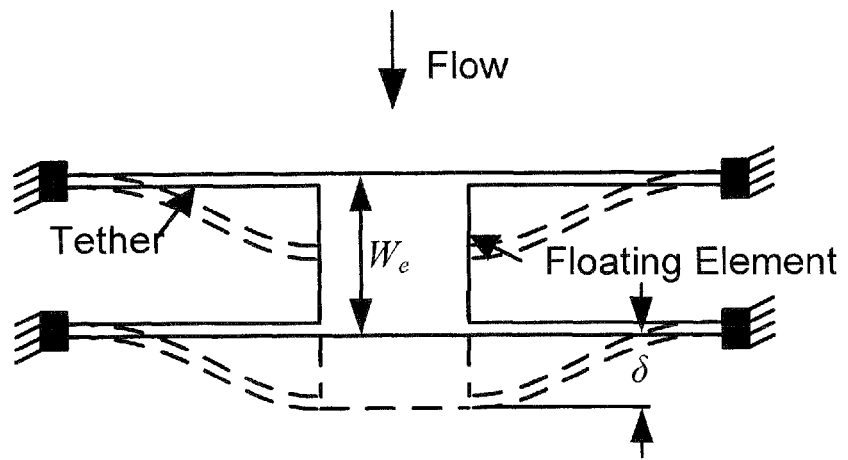
FIGS. 1A and 1B show a basic representation for a floating element sensor.
Figure 1B:
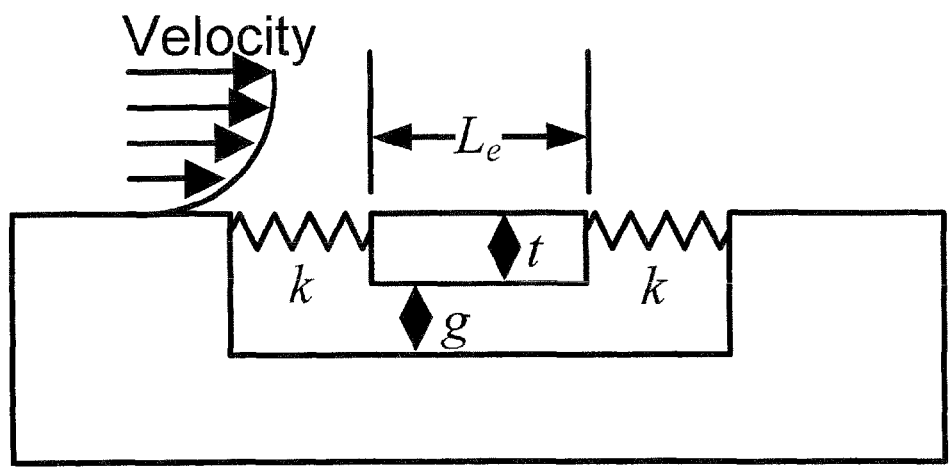

FIGS. 1A and 1B show schematic representations of a floating element sensor. Referring to FIG. 1A, tethers serve as restoring springs. In addition, the shear stress deflects the floating element laterally while a displacement transducer provides a desired output. A number of transduction options are available, including capacitive, optical, piezoresistive, and piezoelectric.

Figure 2A:
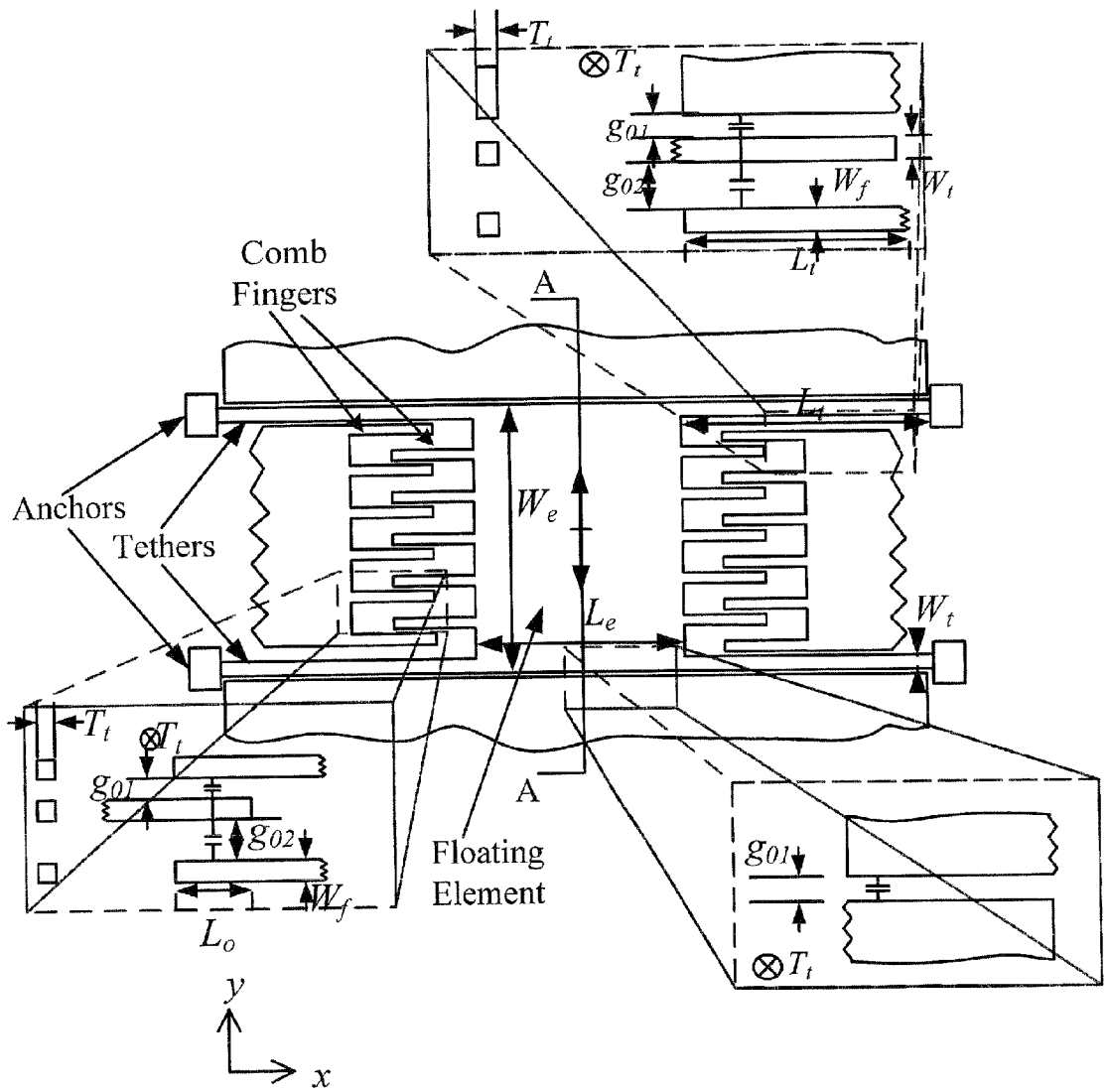
FIGS. 2A and 2B show schematics of geometry of a differential capacitive shear stress sensor according to an embodiment of the present invention.
Figure 2B:
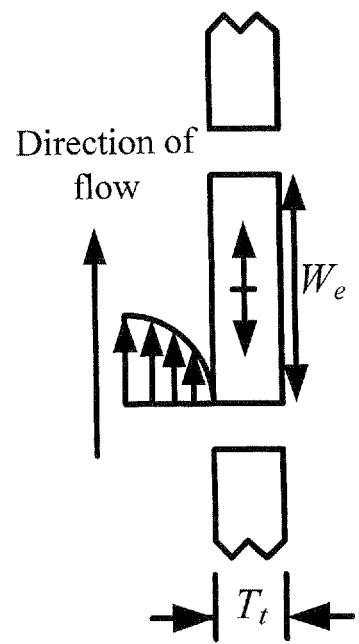

According to embodiments of the present invention, the sensor structure can include interdigitated variable-gap capacitive comb fingers on a floating element. The interdigitated variable-gap capacitive comb fingers can produce an electrical output proportional to the deflection due to shear stress when an appropriate electrical bias is applied. The interdigitated variable-gap capacitive comb fingers can be arranged at one or more sides of the floating element. The arrangement can be single-ended or to provide differential capacitors. FIGS. 2A and 2B show a schematic representation of a sensor in accordance with an embodiment of the present invention, illustrating various dimensions. Deflection of the floating element due to the integrated shear three causes a change in gap between the comb fingers, resulting in a capacitance change (see break-out box 100 of FIG. 2A). There is an additional capacitance change due to the change in gap between the stationary substrate and both the floating element and tethers (see break-out boxes 200 and 300 of FIG. 2A). An appropriate electrical bias establishes a constant charge across the capacitors. The change in capacitance due to deflection results in a voltage change inferred from equation (1):

$$V = \frac{Q|_{constant}}{C}. \tag{1}$$

Here V is the voltage across the capacitors, Q is the charge, which is held on constant by the biasing scheme, and C is the sense capacitance.

According to embodiments of the present invention, the subject sensor can be designed to minimize its sensitivity to pressure. The pressure sensitivity of the sensor has some frequency dependence based on the cavity compliance $C_{cav}$ and the fluidic damping $R_{pressure}$. Here, the $R_{pressure}C_{cav}$ time constant sets the pressure sensitivity cut-off. That is, $$f_{cut\text{-}on_{pressure}} = \frac{1}{2\pi}\sqrt{\frac{1}{R_{pressure}C_{cav}}} \tag{2}$$

(see also FIGS. 9, 18, 22, and 30A). The cut-on frequency is determined by the compliance of the cavity behind the sensor and how much that cavity is vented to the ambient. In microphones, the cut-on frequency is set as low as possible to improve bandwidth. However, for embodiments of the present invention, the cavity and vent are designed to push the cut-on as high as possible in order to inhibit pressure sensitivity. The vent of the cavity can be the gaps between the fingers and the tethers. For embodiments that further include a protective dielectric coating on the sensor, a vent can be created at desired locations and sizes through the protective dielectric coating.

According to certain embodiments, the sensor structure design results in a pair of matched capacitors (ideal) biased by opposite polarity voltages to form a voltage divider. An interface circuit is included to provide signal readout. This measurement scheme is also known as the "differential" capacitance measurement strategy. Identical change in capacitance maintains a balanced bridge failing to produce a voltage at the middle node, while a difference in the sense capacitances results in bridge imbalance and a voltage. The use of the differential measurement scheme can also reduce pressure sensitivity of the subject sensor. This can be accomplished because if the sensor moves in-plane, then the capacitance of one side increases and the capacitance of the other side decreases. In addition, if the sensor moves out of plane, the capacitance of both sides decreases. It is this out-of-plane reaction that can reduce pressure sensitivity.

In an embodiment, a voltage readout circuit can be used to obtain the voltage output, which is proportional to the change in capacitance.

According to an embodiment, the voltage output (directly proportional to shear stress) can be read using a voltage buffer amplifier as the voltage readout circuit. In a specific embodiment as described herein, the voltage buffer amplifier can be the SiSonic™.

The fabrication of the subject sensor can be accomplished using surface micromachining or bulk micromachining. In embodiments utilizing surface micromachining, additive (surface) processes, such as depositing the sensor structures on a handle wafer, can be performed. In embodiments utilizing bulk micromachining, subtractive (bulk) processes, such as etching a pattern into a device layer, can be performed.

FIGS. 3-9 show views for explaining a method of fabricating a sensor according to an embodiment of the present invention. In this embodiment, bulk micromachining is described.

Figure 3:
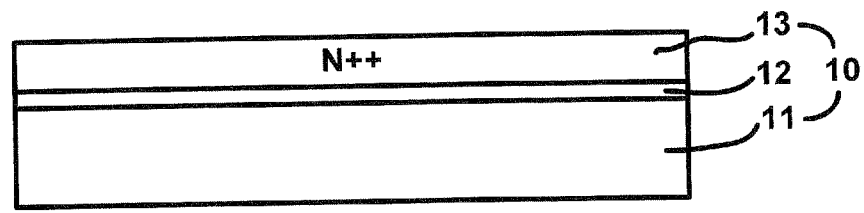
FIGS. 3-9 illustrate a method of fabricating a sensor according to an embodiment of the present invention.

FIG. 3 shows a cross-sectional view of an SOI wafer 10. In an embodiment, the wafer 10 can include a lightly doped bulk substrate 11, a buried oxide layer 12, and a highly doped device layer 13 on the oxide layer 12. A specific embodiment can utilize a SOT wafer with a 500 μm $Si_{FZ}$ (float zone) substrate, a 2 μm oxide layer, and a 45 μm highly doped silicon layer. The highly doped silicon layer 13 can be doped with, for example, n-type impurities. In another specific embodiment, the SOI wafer can include Electrical Through Wafer Interconnects (ETWI) for ease of backside connections to the sensor.

A two mask process can be used to fabricate the subject sensor from the SOT wafer 10. It should be noted that though the method of fabricating the sensor is described with respect to an SOI substrate, embodiments are not limited thereto. For example, the two mask process can be used to fabricate the subject sensor from other types of substrates. The substrates can be for example, a substrate having a conductive device layer and an insulator handle layer. In one embodiment, the conductive device layer can be formed of semiconductor. In another embodiment, the conductive device layer can be formed of metal. In a further embodiment, the conductive device layer can be formed of a polymer coated with metal. The insulator handle layer can be a layer of glass or plastic on the conductive device layer (and used in place of the handle wafer of the SOI). In a specific embodiment, insulator handle layer can be formed of Pyrex, which can decrease the parasites as compared to the float zone silicon substrate of certain SOT substrates.

Figure 4A:
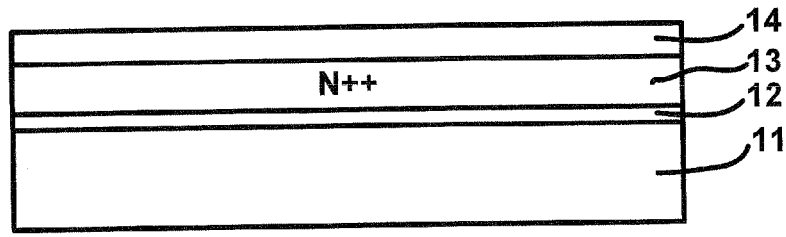
Figure 4B:
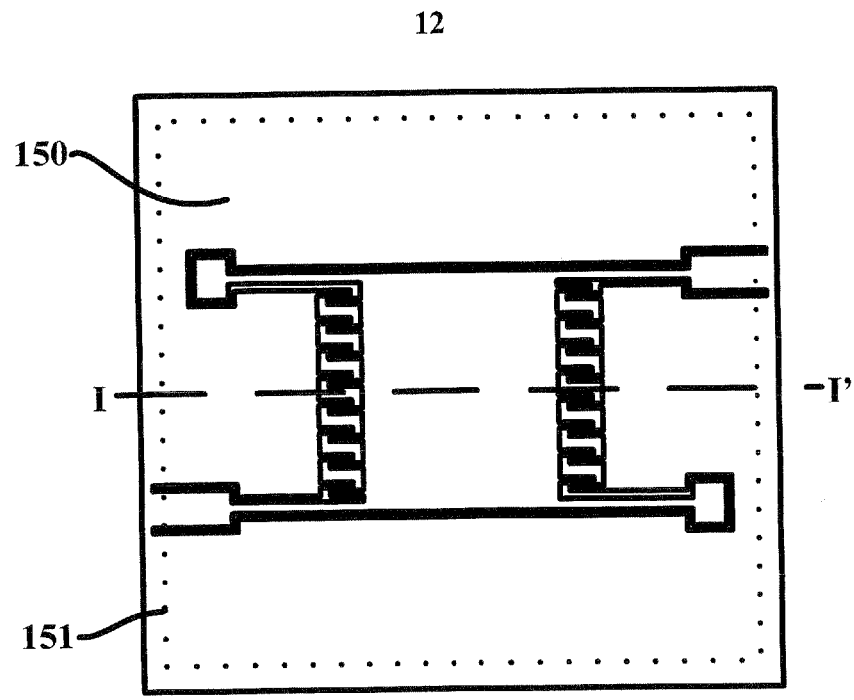
Figure 4C:
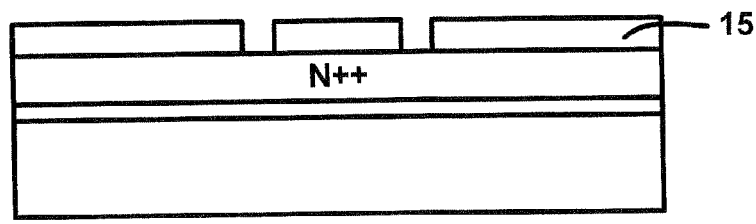

A first etching process can be performed to form features, including comb fingers and tethers of the device using a first mask process as shown in FIGS. 4A-4C. According to an embodiment, a photoresist 14 can be coated on the device layer 13. Then a first mask 150 such as shown in FIG. 4B can be used to pattern the photoresist 14. The first mask 150 can be used to define all the sensor features/structures. The sensor features/structures can include single ended or differential capacitors, and both may be formed during the same fabrication process. FIG. 4C shows a cross-section through line I-I' (FIG. 4B) of a first photoresist pattern 15 formed using the first mask 150. The first photoresist pattern 15 can be formed through exposure and development processes of the first mask process.

Figure 5:
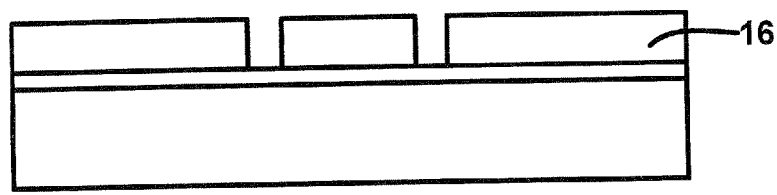

Referring to FIG. 5, the device layer 13 can be etched using the first photoresist pattern 15 as an etch mask to form the features of the device in the device layer 13 (the etched features referred to in FIG. 5 as patterned device layer 16). The etching process can be a deep reactive ion etch (DRIE). The oxide layer 12 may be used as an etch stop during the DRIE. The etching process can be performed to form high aspect ratio capacitive gaps between the features of the device.

Figure 6:
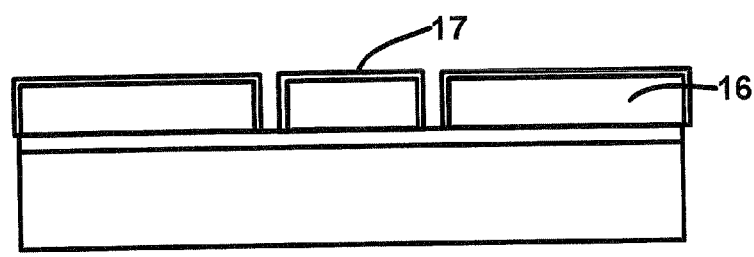

Referring to FIG. 6, a conductive material 17 can be formed on the patterned device layer 16. In an embodiment, the conductive material can be a metal plated directly onto the patterned device layer 16. The plated metal can be used for capacitive passivation. In a specific embodiment, the metal 17 can be nickel. The nickel can be electroplated to a thickness of, for example, about 0.2 μm.

Figure 7A:
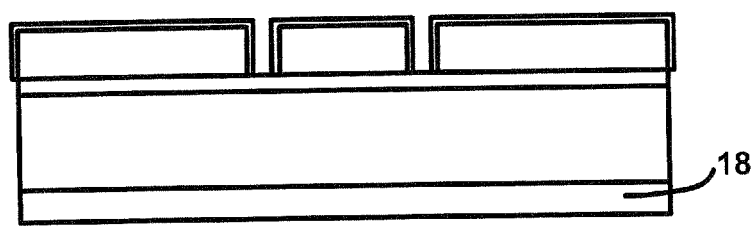
Figure 7B:
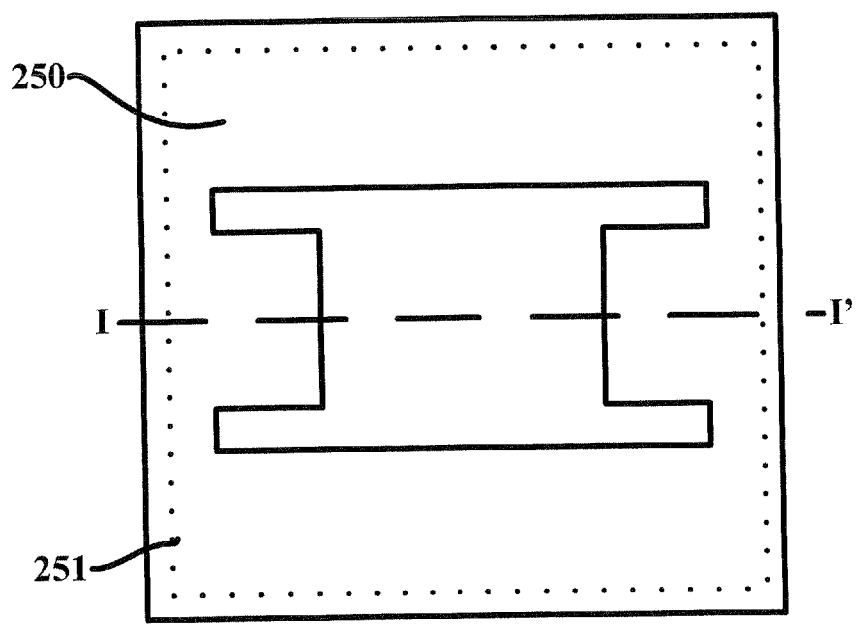
Figure 7C:
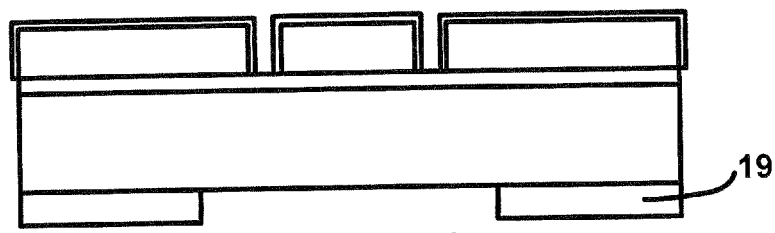

Next, a front to back mask alignment can be performed and a second etching process can be performed to create a backside cavity. The second etching process can be performed using a second mask process as shown in FIGS. 7A-7C. The second mask can define the sensor structure release. According to an embodiment, a photoresist 18 can be coated on the bulk substrate 11 at the backside of the wafer 10. Then a second mask 250 such as shown in FIG. 7B can be used to pattern the photoresist 18. FIG. 7C shows a cross-section through line I-I' (FIG. 7B) of a second photoresist pattern 19 formed using the second mask 250. The second photoresist pattern 19 can be formed through exposure and development processes of the second mask process.

Figure 8:
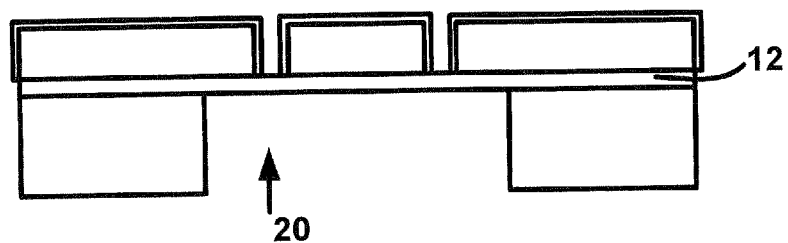

Then, referring to FIG. 8, the bulk substrate 11 at the back side of the wafer 10 can be etched using the second photoresist pattern 19 as an etch mask to form the backside cavity 20 for the device. The etching process can be a DRIB. The buried oxide layer 12 can be used as the etch stop during the DRIE.

Figure 9:
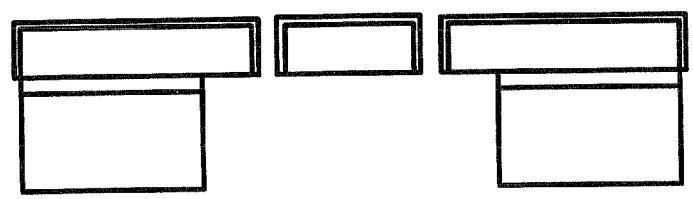

Referring to FIG. 9, a wet oxide etch can be performed to remove exposed regions of the buried oxide layer 12. In one embodiment, the wet oxide etch can be performed using HF in a specific embodiment a 20 min BOE can be performed followed by a super critical dry to inhibit stiction.

In a further embodiment, a protective dielectric coating can be used to protect the sensing area of the device from the flow of an external ambient or atmosphere. The protective dielectric coating can be formed of an insulative material including, but not limited to an oxide, a nitride, a polymer, or a combination thereof. In a specific embodiment, the dielectric coating can be a polymer such as polyimide or PDMS. The protective dielectric can be formed at a thickness that protects the surfaces while still allowing the structures of the sensor to move. In embodiments including the protective dielectric coating, a vent for the backside cavity 20 can be introduced to allow the cavity to be vented to the atmosphere through the side or from the top of the sensor device.

FIGS. 10-18 illustrate an embodiment that incorporates the protective dielectric and vent. Elements and steps similar to those described with respect to FIGS. 3-9 will be referred to using the same reference numbers.

Figure 10A:
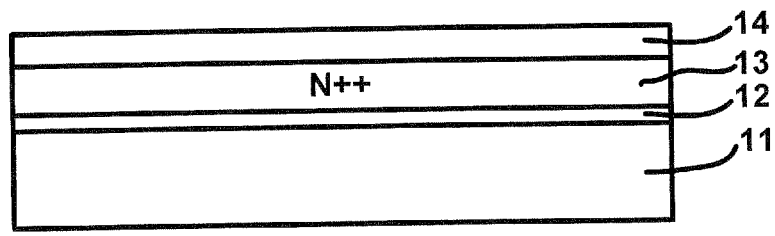
FIGS. 10-18 illustrate a method of fabricating a sensor according to an embodiment of the present invention.
Figure 10B:
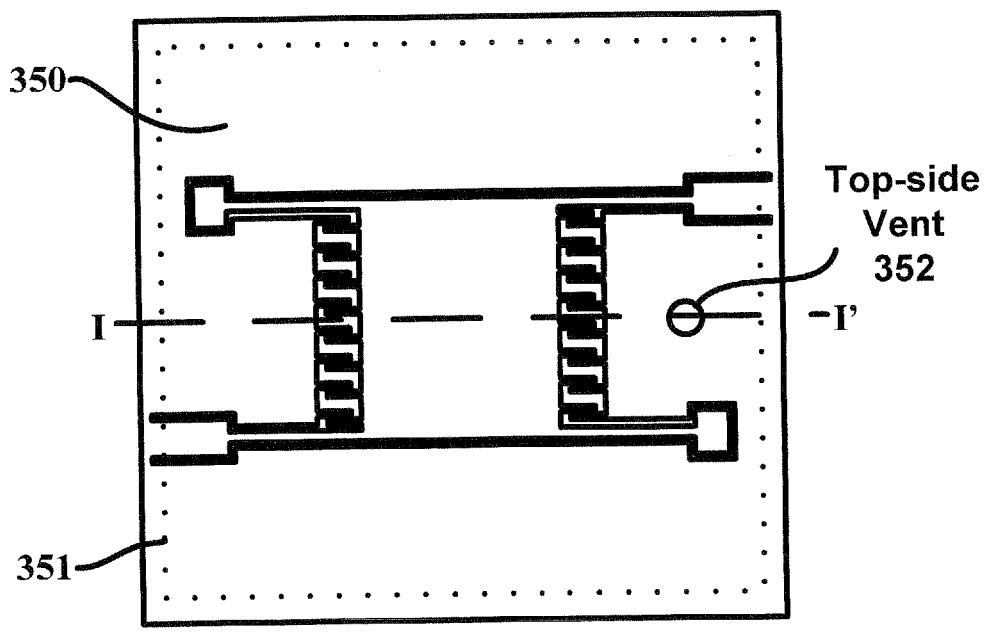
Figure 10C:
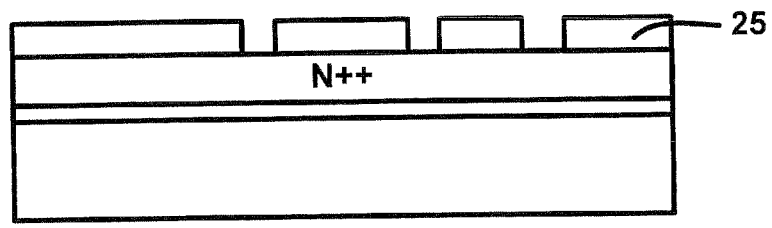

According to an embodiment, the first mask 350 can include a feature for a top side vent 352 such as shown in FIG. 10B. A first etching process can be performed using a first mask process as shown in FIGS. 10A-10C. According to an embodiment, a photoresist 14 can be coated on the device layer 13. Then, a first mask 350 such as shown in FIG. 10B can be used to pattern the photoresist 14. FIG. 10C shows a cross-section through line I-I'(FIG. 10B) of a first photoresist pattern 25 formed using the first mask 350. The first photoresist pattern 25 can be formed through exposure and development processes of the first mask process. Here, the first photoresist pattern 25 exposes a portion of the device layer 13 corresponding to where the top side vent will be disposed. It should be noted that while the feature for a top side vent 352 is shown having a circular cross-sectional shape, embodiments are not limited thereto. For example, the top side vent can have a polygonal cross-section.

Figure 11:
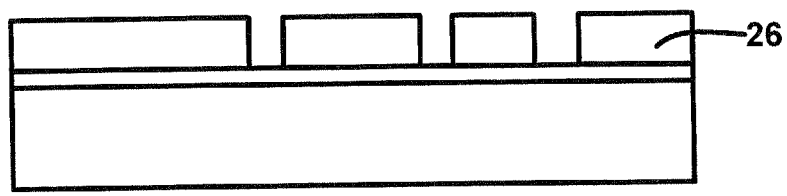

Referring to FIG. 11, the device layer 13 can be etched using the first photoresist pattern 25 as an etch mask to form the features of the device in the device layer 13 (the etched features referred to in FIG. 11 as patterned device layer 26).

Figure 12:
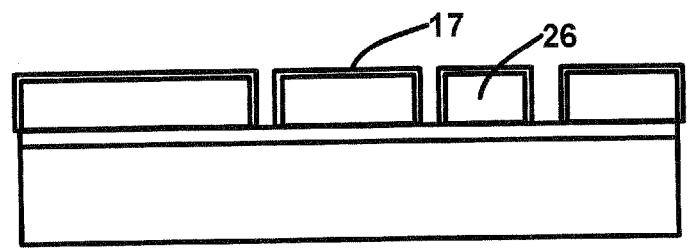

Referring to FIG. 12, a conductive material 17 can be formed on the patterned device layer 26.

Figure 13A:
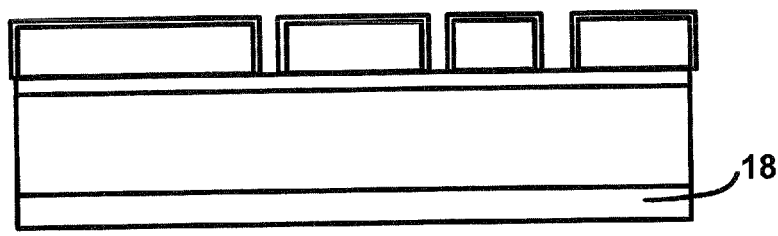
Figure 13B:
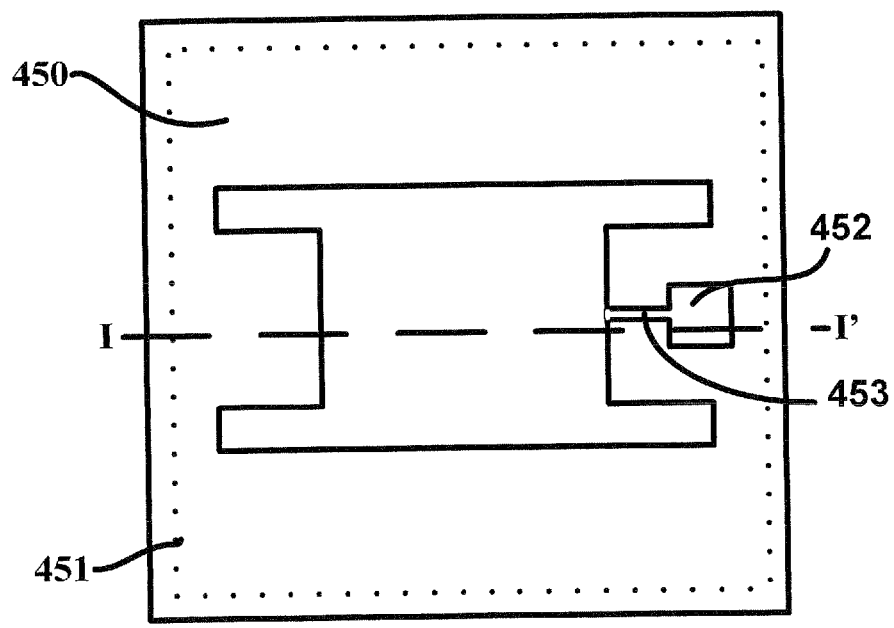
Figure 13C:
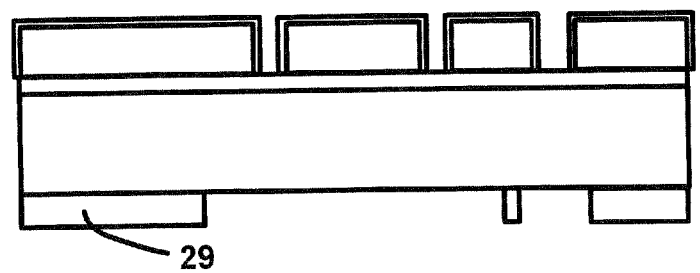

Next, a front to back mask alignment can be performed and a second etching process can be performed to create a backside cavity. The second etching process can be performed using a second mask process as shown in FIGS. 13A-13C. The second mask can define the sensor structure release. According to an embodiment, a photoresist 18 can be coated on the bulk substrate 11 at the backside of the wafer 10. Then a second mask 450 such as shown in FIG. 13B can be used to pattern the photoresist 18. The second mask 450 provides a pattern 452 and vent line 453 for enabling the vent to reach the cavity. Although the vent line 453 is shown as being substantially narrower than the pattern 452, embodiments are not limited thereto. In addition, pattern 452 can have any desired cross-sectional shape, including but not limited to polygonal, circular, and elliptical. FIG. 13C shows a cross-section through line I-I' (FIG. 13B) of a second photoresist pattern 29 formed using the second mask 450.

Figure 14:
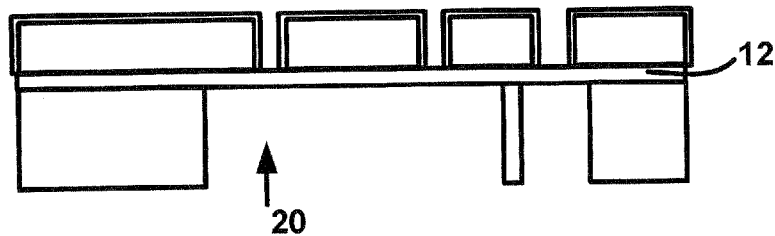

Then, referring to FIG. 14, the bulk substrate 11 at the back side of the wafer 10 can be etched using the second photoresist pattern 29 as an etch mask to form the backside cavity 20 and vent line (not shown in the cross-section) for the device.

Figure 15:
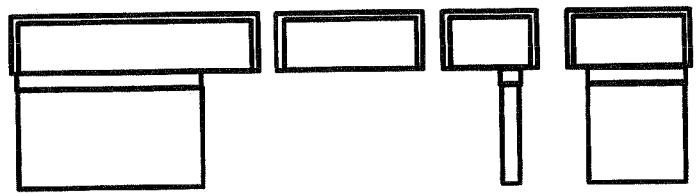

Referring to FIG. 15, a wet oxide etch can be performed to remove exposed regions of the buried oxide layer 12.

Figure 16:
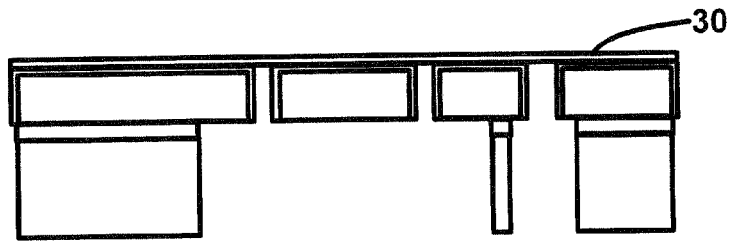
Figure 17:
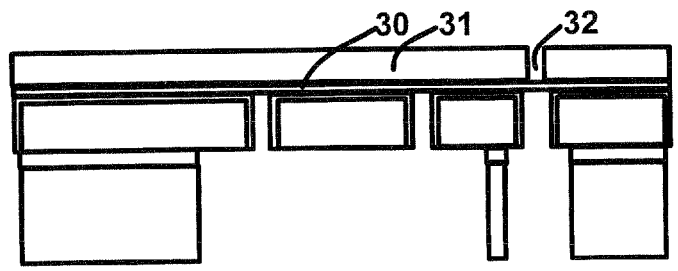
Figure 18:
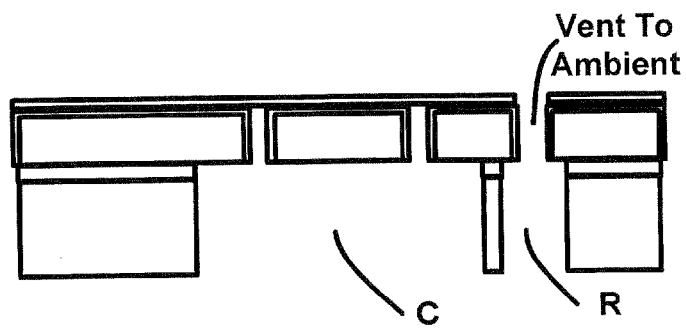

Referring to FIG. 16, a protective dielectric 30 can be formed on the top side of the wafer 10. An etch mask 31 can be formed on the protective dielectric 30, exposing a vent region 32 as shown in FIG. 17. Then, referring to FIG. 18, the protective coating 30 can be etched using the etch mask 31 to open the vent to the ambient. In FIG. 18, the C represents cavity compliance $C_{cav}$ and the R represents dampening $R_{pressure}$.

FIGS. 19-22 illustrate another embodiment that incorporates the protective dielectric and vent. Here, a side vent is illustrated. Elements and steps similar to those described with respect to FIGS. 3-9 will be referred to using the same reference numbers. Furthermore, the method shown in FIGS. 19-22 can begin after the step illustrated in FIG. 7A.

Figure 19A:
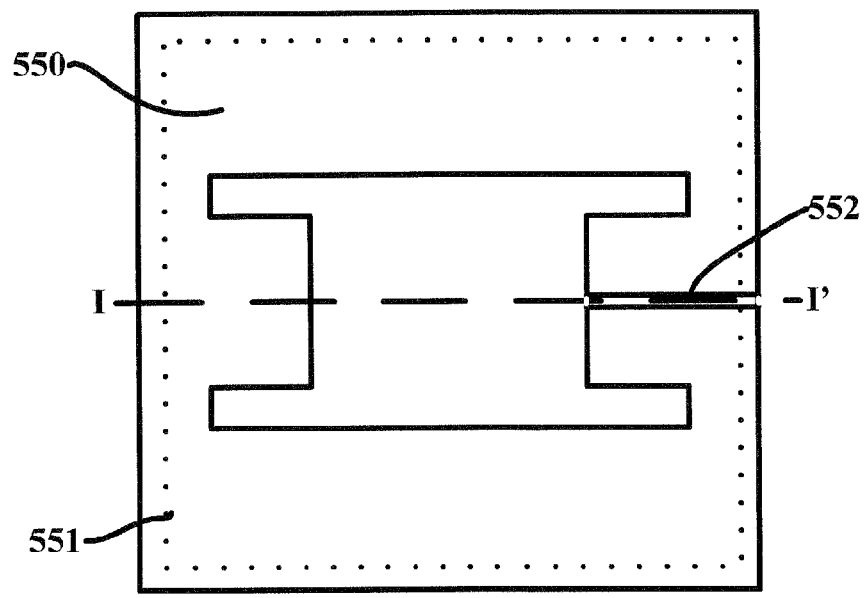
FIGS. 19-22 illustrate a method of fabricating a sensor according to an embodiment of the present invention.
Figure 19B:
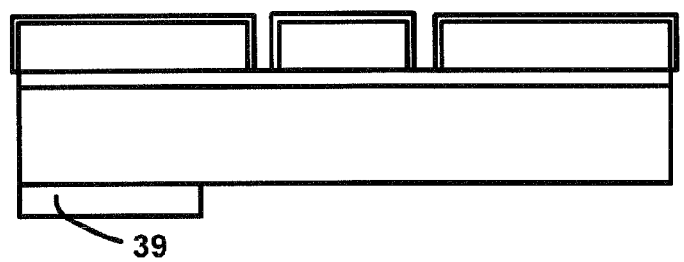

Accordingly, a second etching process can be performed using a second mask process as shown in FIGS. 19A and 19B after coating a photoresist 18 on the bulk substrate 11 at the backside of the wafer 10 as shown in FIG. 7A. Here, a second mask 550 such as shown in FIG. 19A can be used to pattern the photoresist 18. The second mask 550 provides a vent line 452 for enabling the vent to reach the cavity from a side of the sensor. FIG. 19B shows a cross-section through line I-I" (FIG. 19A) of a second photoresist pattern 39 formed using the second mask 550. It should be noted that the line I-I' in FIG. 19A passes through the vent line 552.

Figure 20:
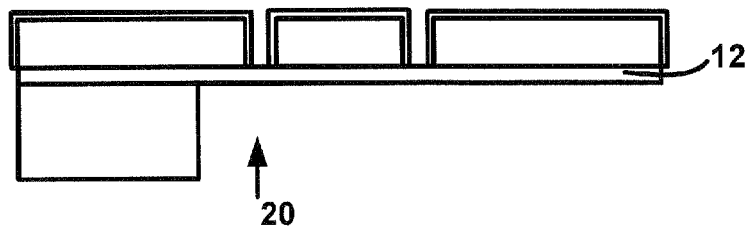

Then, referring to FIG. 20, the bulk substrate 11 at the back side of the wafer 10 can be etched using the second photoresist pattern 29 as an etch mask to form the backside cavity 20 and vent line 40 for the device.

Figure 21:
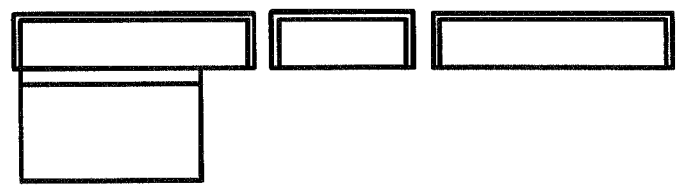

Referring to FIG. 21, a wet oxide etch can be performed to remove exposed regions of the buried oxide layer 12.

Figure 22:
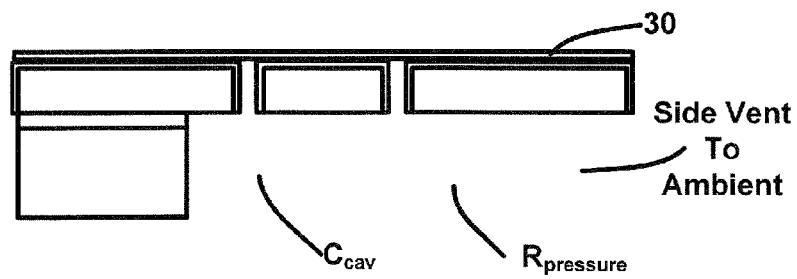

Then, referring to FIG. 22, a protective dielectric 30 can be formed on the top side of the wafer 10. In FIG. 22, the C represents cavity compliance $C_{cav}$ and the R represents dampening $R_{pressure}$.

After release of sensor components through performing the wet oxide etch, the wafer can be diced to electrically isolate capacitors. The dicing can follow the dice lines 151, 251, 351, 451, and 551 indicated in FIGS. 4B, 7B, 10B, 13B, and 19A. Prior to dicing all surfaces may be electrically connected for plating (e.g., for the metal passivation). As described above, the plating can be performed before forming the protective coating. Furthermore, although a metal plating process has been described above with respect to the conductive material formed on the patterned device layer, embodiments are not limited thereto. The metal passivation can be formed through any suitable metal deposition technique, including but not limited to electroplating, sputtering, evaporation electroless plating, and chemical vapor deposition.

Figure 24A:
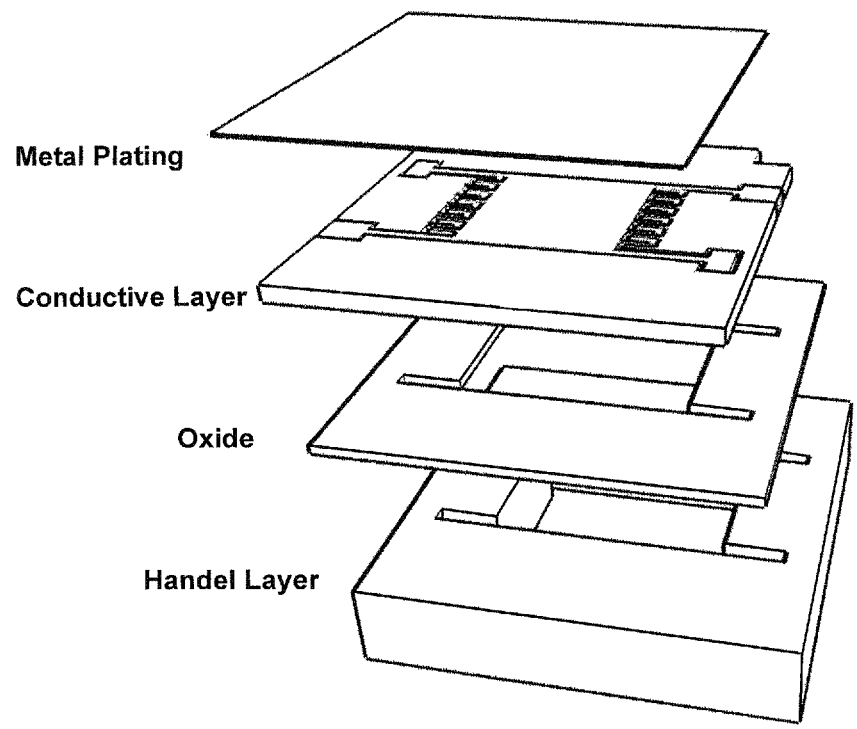
FIGS. 24A and 24B show a perspective view of a sensor according to an embodiment of the present invention.
Figure 24B:
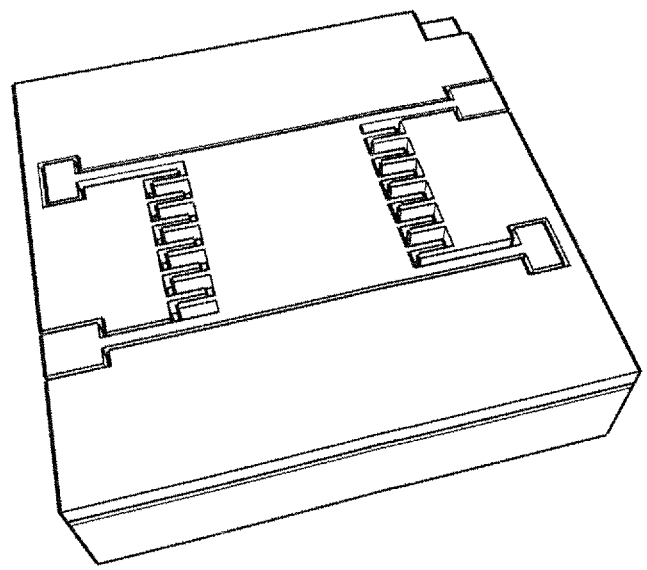
Figure 25A:
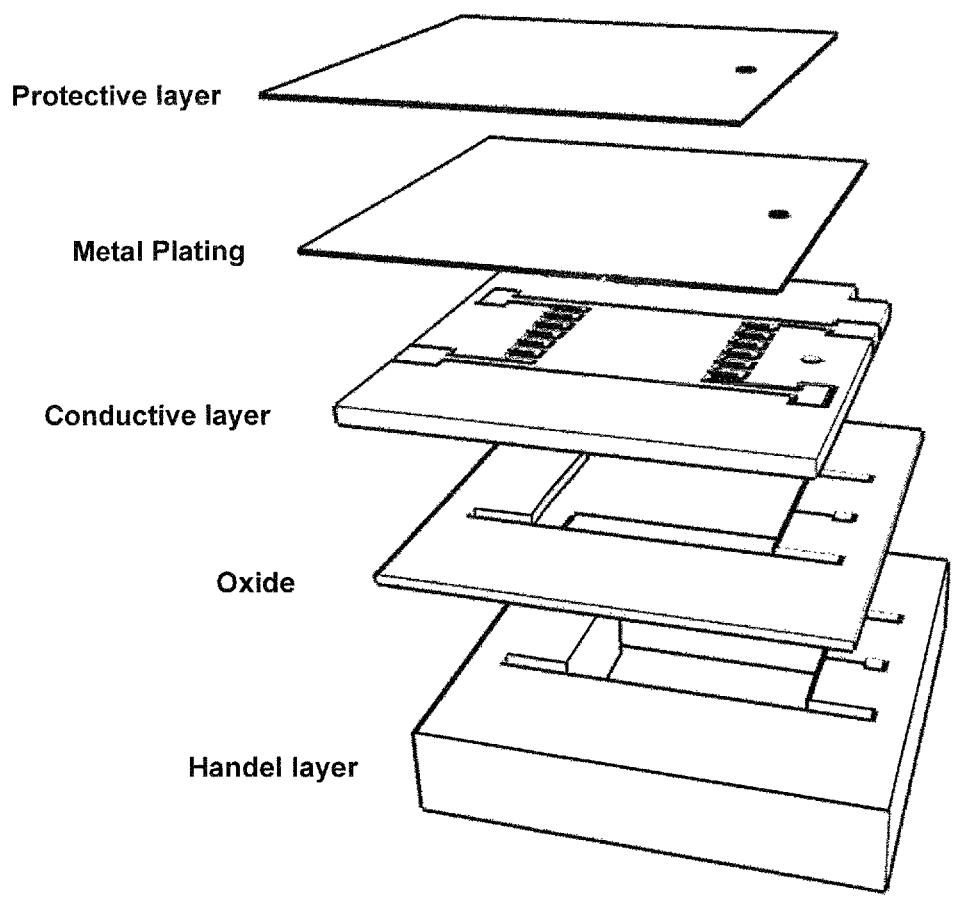
FIGS. 25A and 25B show a perspective view of a sensor having a top vented protective layer according to an embodiment of the present invention.
Figure 25B:
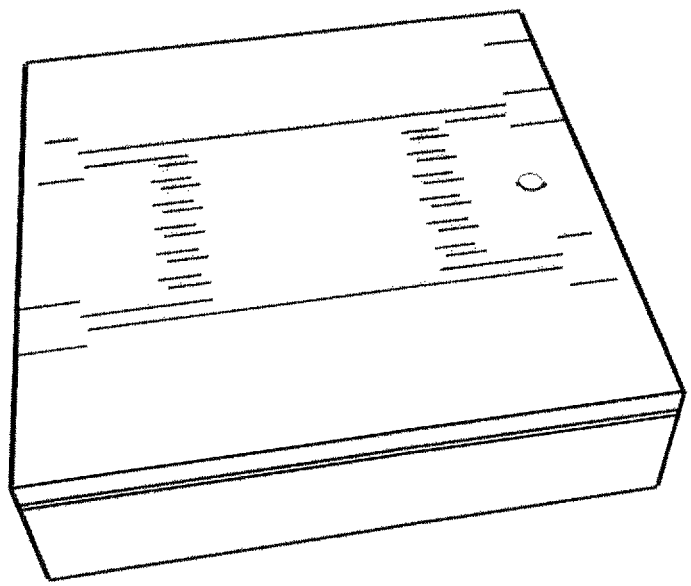
Figure 26A:
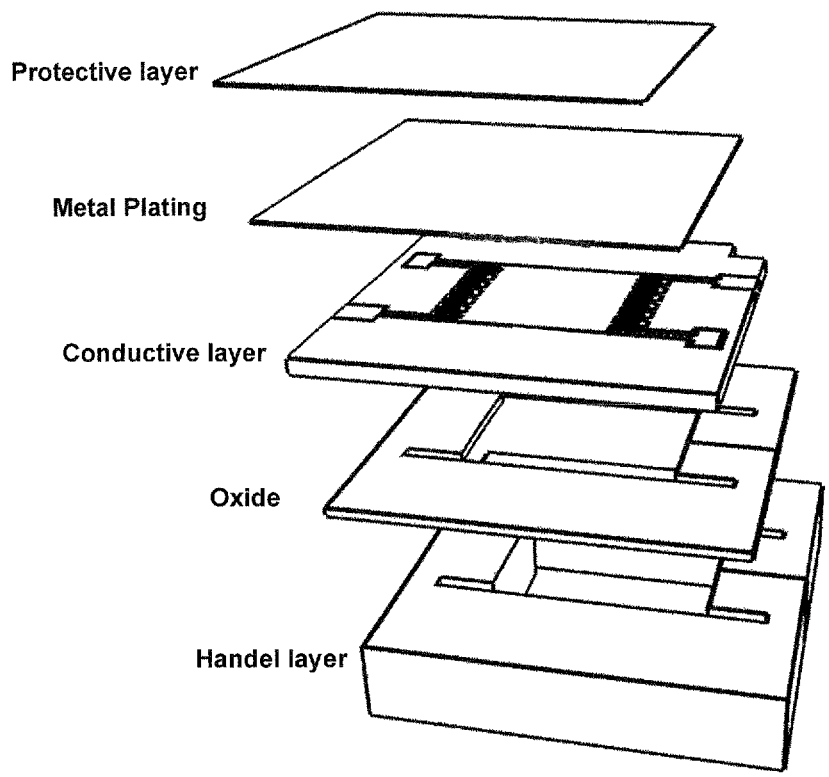
FIGS. 26A and 26B show a perspective view of a sensor having a side vent and protective layer according to an embodiment of the present invention.
Figure 26B:
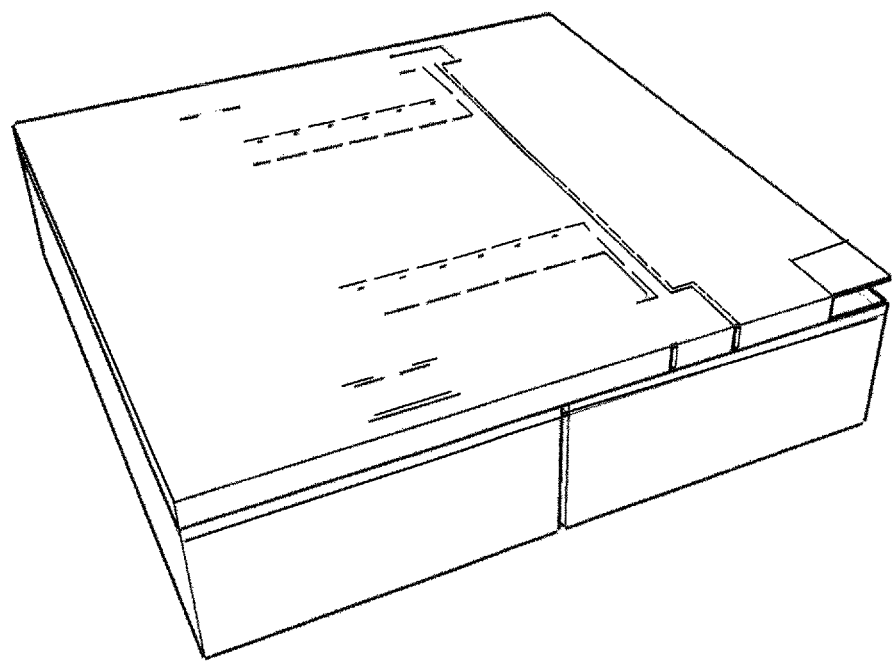

FIGS. 24A-24B, 25A-25B, and 26A-26B show perspective views of the devices formed in accordance to the methods described above. FIGS. 24A and 24B show a sensor formed according to the method described with respect to FIGS. 3-9; FIGS. 25A and 25B show a sensor formed according to the method described with respect to FIGS. 10-18; and FIGS. 26A and 26B show a sensor formed according to the method described with respect to FIGS. 19-22.

According to embodiments, metal passivation can be performed with respect to the surfaces to inhibit charge accumulation.

The metal passivation technique can provide an efficient and cost effective method for passivating the surfaces of the subject electrostatic sensors and actuators. The technique used on SOI devices can ensure that only the sensor/actuator surface is passivated, and not the substrate silicon. By utilizing the metal passivation, drift issues in micro-scale electrostatic devices can be mitigated.

Figure 23:
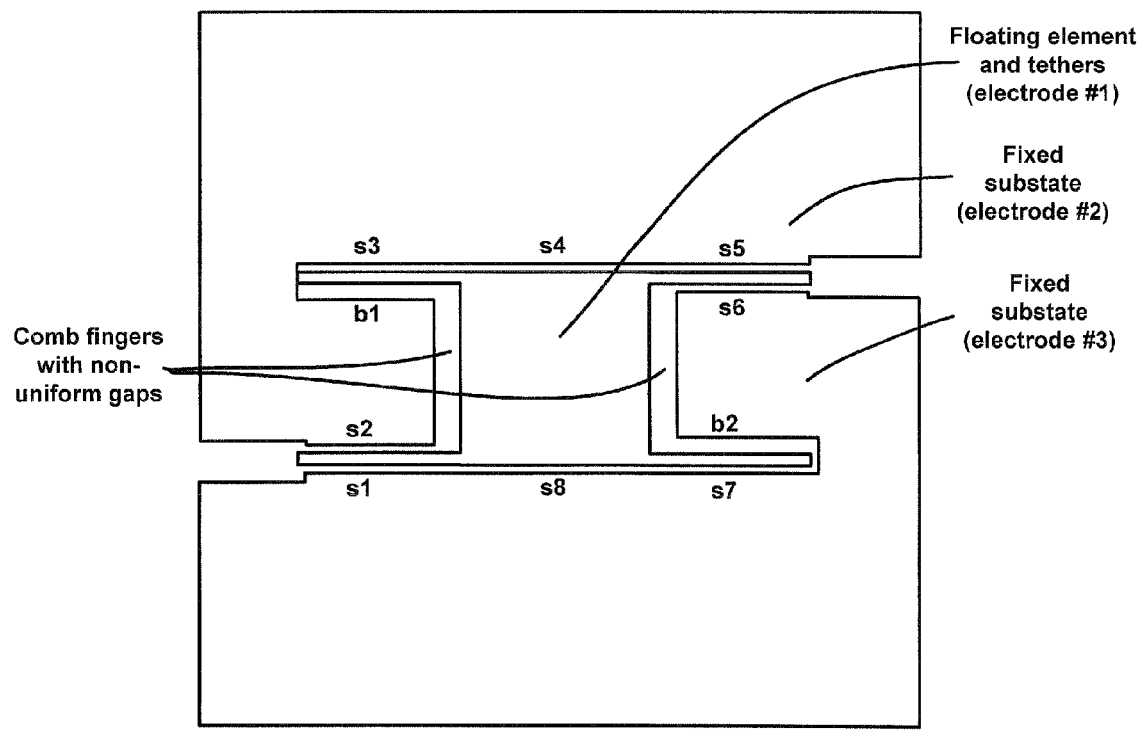
FIG. 23 shows a plan view of a floating element sensor in accordance with an embodiment of the present invention.

A plan view of a sensor element in accordance with an embodiment of the present invention is shown in FIG. 23. The sensor can be considered to have a plurality of electrodes due to the formation of a conductive material in a fabrication process such as shown in FIG. 6. In a specific embodiment, the sensor can have a first electrode defined by the floating element and the tethers, a second electrode defined by a portion of the fixed substrate also including one side of comb fingers, and a third electrode defined by the other portion of the fixed substrate that includes the other side of comb fingers.

Although not drawn in the figure, comb fingers are disposed between the floating element and the fixed substrate. The comb fingers can be provided in accordance with the mask 150 shown in FIG. 4B. The comb fingers are provided having non-uniform gaps. This can be accomplished with offset, regularly spaced comb fingers. The offset can be provided such that the fingers of the floating element and the fingers of the fixed substrate are not equidistant from each other. In another embodiment, the fingers can be irregularly spaced. In certain embodiments using a differential measurement scheme, the tethers and the comb fingers on one side of the sensor can be asymmetrically disposed with respect to the tethers and comb fingers on the other side of the sensor. In a particular embodiment, a combination of relatively small sized gaps and relatively large sized gaps can be arranged between the floating element, tethers, and fixed substrate. Referring to FIG. 23, side surface gaps s1, s2, s3, s5, and s7 between the tethers and the fixed substrates can be relatively small. In addition, side surface gaps s4 and s8 between an ends (non-fingered sides) of the floating element and the fixed substrates can be relatively small. Then, side surface gaps b1 and b2 between the tethers and the fixed substrates can be relatively large. The large surface gaps b1 and b2 can be equal to each other or can have different gap distances. Further, one or more of the small side surface gaps s1, s2, s3, s4, s5, s7 and s8 can have the same gap distances. In a specific embodiment, the small side surface gaps are all equal to each other and the large side surface gaps are equal to each other.

In certain embodiments, a rotational or translational symmetry can be provided between the two sides.

In one embodiment, a sensor is provided having a low minimum detectable signal (MDS) or $\tau_{min}$, which is defined as the ratio of the electronic noise floor (V) to the sensitivity (V/Pa). A local optimization technique can be employed to minimize the MDS while satisfying bandwidth and linearity requirements.

The following describes a system-level physical model that can be used in the design of the subject sensor. The system-level physical model described below is divided into three parts: a mechanical model, an electrical model, and an equivalent electromechanical circuit model.

For mechanical modeling, a structural model of the sensor is provided that relates the wall shear stress, $\tau_w$, to the floating element deflection, $\delta$. The structural design directly influences the mechanical sensitivity, bandwidth, and the linearity of the dynamic response. As shown in FIG. 2A, an embodiment of the subject sensor can include a rigid floating element suspended over a cavity by four tethers that act as restoring springs. A flow over the sensor surface results in a shear force on the floating element, comb fingers, and the tethers.

Figure 27:
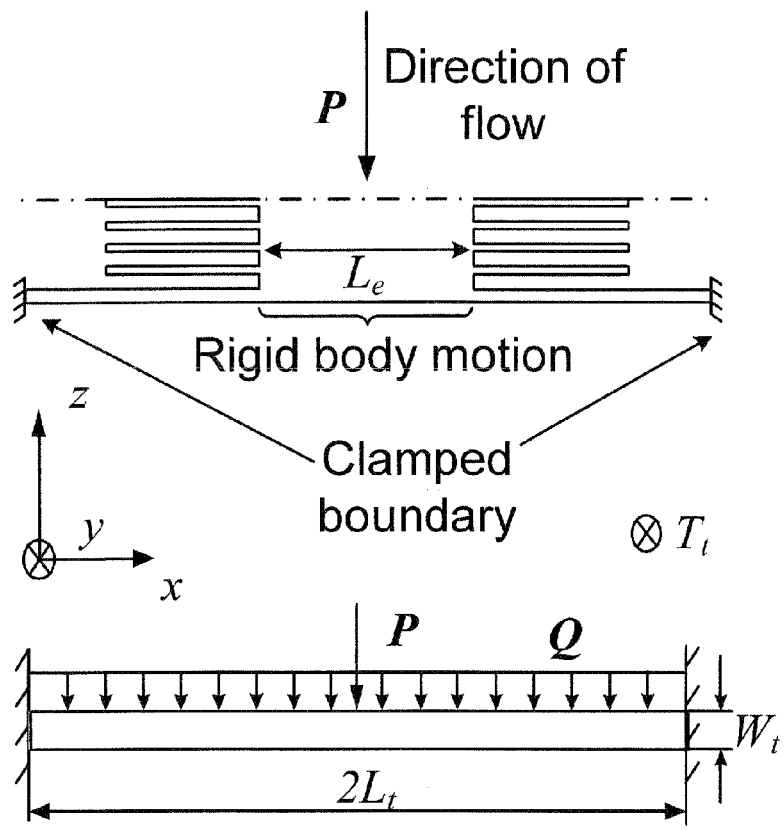
FIG. 27 shows a structural model for an embodiment of the subject sensor.

Referring to FIG. 27, for mechanical modeling of the subject sensor, a model similar to that described by Schmidt et al. in "Design and Calibration of a Micromachined Floating-Element Shear-Stress Sensor" (*Transactions on Electronic Devices*, Vol. Ed-35, No. 1988, pp. 750-757) can be used, where the tethers can be modeled as clamped-clamped beams, and the floating element can be considered rigid. The comb fingers can also be considered rigid, and their effect is included in the analysis.

The integrated shear force resulting from $\tau_w$ results in the floating element deflection $\delta$, which is estimated using the Euler Bernoulli beam theory for small deflections as provided in equation (3).

$$\delta = \frac{\tau_w W_e L_e}{4ET_t}\left(1 + \frac{NW_f L_f}{W_e L_e} + 2\frac{W_t L_t}{W_e L_e}\right)\left(\frac{L_t}{W_t}\right)^3. \tag{3}$$

Here, $L_e$ and $W_e$ are the length and width of the floating element; $L_t$ and $W_t$ are length and width of the tethers; $L_f$ and $W_f$ are the length and width of the comb fingers; $T_t$ is the thickness of the floating element, tethers and comb fingers; N is the number of comb fingers; and E is the Young's modulus of the sensor material (in this case silicon). In the summation in equation (3), the first term accounts for the floating element, the second term for the comb fingers, and the final term for the tethers. The structure can be designed such that $T_t \gg W_t$ to ensure higher stiffness in the transverse direction to minimize out-of-plane motion.

Accordingly, in a preferred embodiment, the thickness of the floating element is made much larger than the width of the tethers.

For electrical modeling, the comb fingers of the sensor shown in FIG. 2A can be modeled as parallel-plate capacitors.

Figure 28:
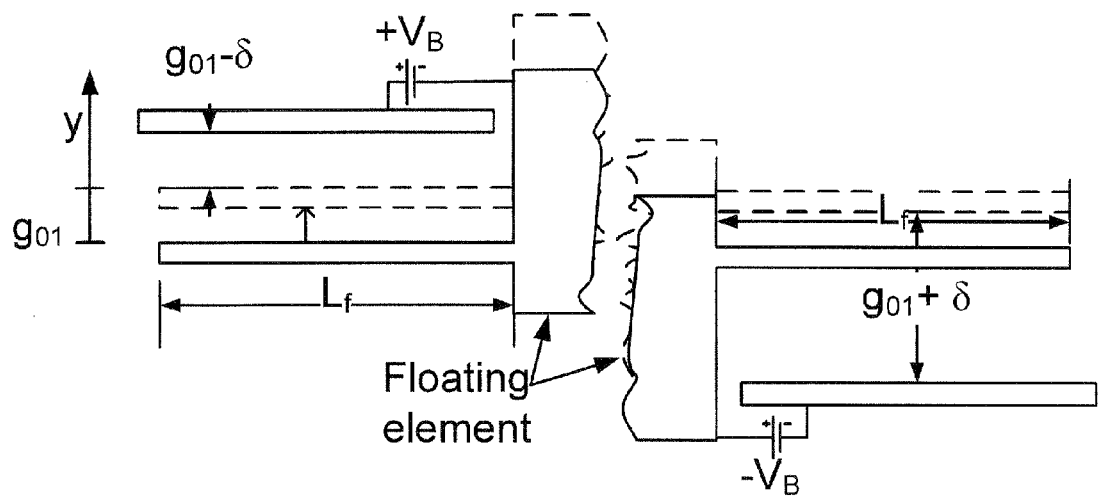
FIG. 28 shows an electrical model for an embodiment of the subject sensor.

For example, as shown in FIG. 28, which illustrates a set of two comb finger capacitors on either side of the floating element, the overlapping planar surfaces formed by the sensor structure are modeled as simple parallel-plate capacitors. The two sides of the floating element having the comb finger capacitors provide a differential pair. Assuming that the electrodes are perfect electrical conductors, the electrical field is normal to the conductors, capacitance change from the fringing electrical fields are negligible, and only nominally large overlapping planar surfaces contribute to sensor capacitance, the nominal capacitance for a single capacitor of the differential pair is given as equation (4):

$$C_0 = \varepsilon T_t\left[\frac{3L_{teff} + L_e + \frac{(N-1)}{2}L_f}{g_{01}} + \frac{L_{teff} + \frac{(N-1)}{2}L_f}{g_{02}}\right], \tag{4}$$

where $\varepsilon$ is the dielectric permittivity of the medium (air) and $g_{01}$ & $g_{02}$, which are shown in break-out box 100 of FIG. 2A illustrating capacitance of comb-finger elements, are the asymmetric gaps in the comb fingers that help to achieve higher sensitivity. According to an embodiment, $g_{01} < g_{02}$. Although not specifically described here, break-out box 200 of FIG. 2A illustrates capacitance between a tether and both a stationary substrate and a comb finger; and break-out box 300 of FIG. 2A illustrates capacitance between the floating element and the stationary substrate.

An effective tether length $L_{teff}$ is used to model the tethers as parallel plate capacitors while accounting for the non-uniform gap due to the bending of the tethers and numerically calculated as equation (5):

$$L_{teff} = \frac{L_t}{2}. \tag{5}$$

Figure 29:
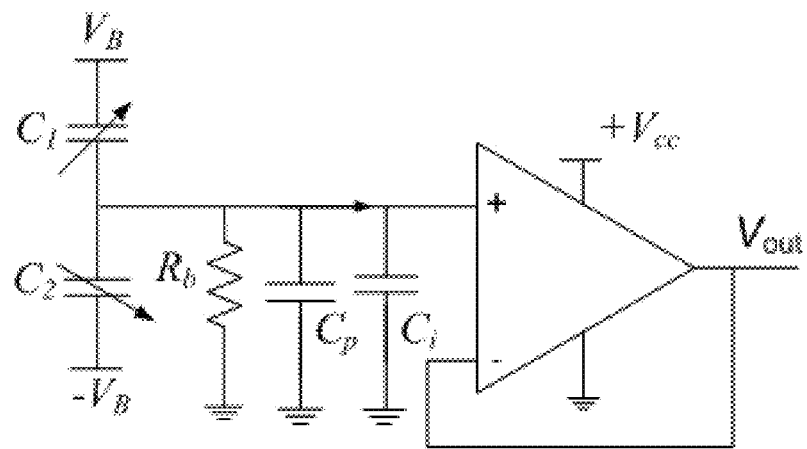
FIG. 29 shows a schematic of the differential capacitance readout scheme using a voltage amplifier in accordance with an embodiment of the present invention.

According to embodiments, the sensor structure design results in a pair of matched capacitors (ideal) biased by opposite polarity voltages to form a voltage divider as shown in FIG. 29. An interface circuit is included to provide signal readout.

The voltage output (directly proportional to shear stress) can be read using a voltage buffer amplifier. The voltage amplifier can utilize a constant charge biasing scheme. Referring to FIG. 29, a circuit representation for the differential capacitance readout scheme is shown. The bias resistor $R_b$ sets the dc operating point of the amplifier, $C_p$ is the parasitic capacitance, and $C_i$ is the input capacitance of the amplifier. The variable capacitors $C_1$ and $C_2$ are the matched sensor capacitances as "seen" at the input of the interface circuit. The bias voltages applied to $C_1$ and $C_2$ to are equal in magnitude and opposite in polarity. The output voltage for this configuration is as provided in equation (6):

$$V_{out} = V_B \frac{C_1 - C_2}{C_1 + C_2 + C_p + C_i}. \tag{6}$$

For in-plane displacement of the floating element in the y-direction, $C_1$ increases ($C_0 + \Delta C$) and $C_2$ decreases ($C_0 - \Delta C$)

or vice-versa. This results in a differential output voltage as shown in equation (7):

$$V_{out}|_{differential} = \frac{\Delta C}{C_0 + (C_p + C_i)/2} \quad (7)$$

Figure 30A:
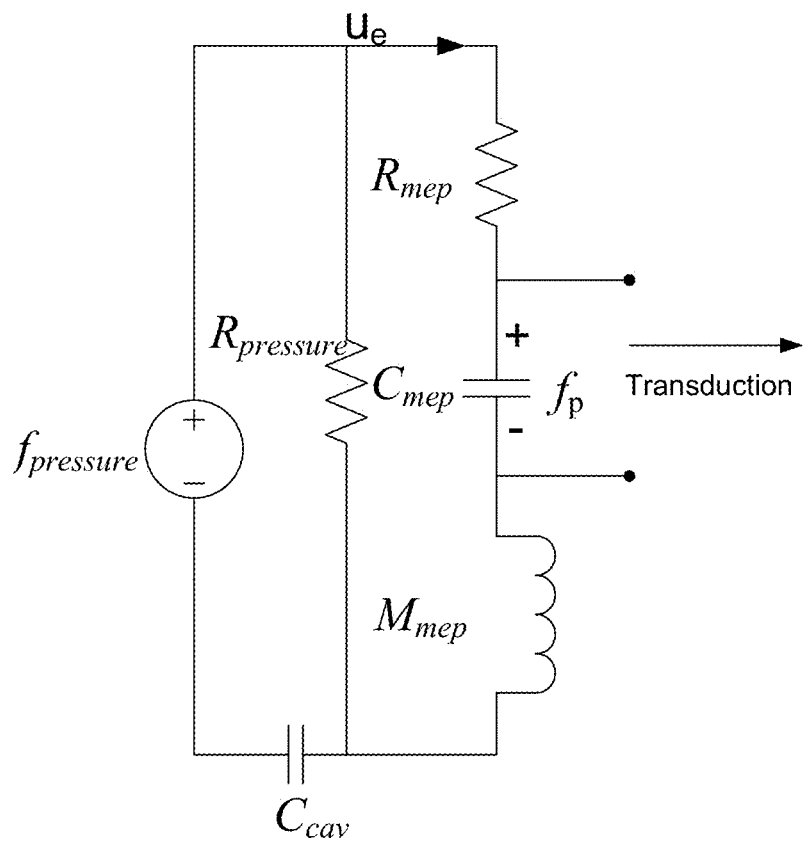
FIGS. 30A and 30B show schematics of equivalent circuits for the differential capacitive shear stress sensor according to an embodiment of the present invention.

Out-of-plane motion in the z-direction, if any, results in the increase/decrease of $C_1$ and $C_2$ simultaneously ($C_0 \pm \Delta C$), failing to produce a voltage at the amplifier input. Deflections from forces in the x-direction (along tether length) are considered negligible due to high stiffness (with respect to the tether) in that direction. Output due to pressure (force in the z-direction) is minimized using the sensor structure, damping and cavity compliance combination ($R_{pressure}C_{cav}$), cavity stiffening and the common mode signal attenuation achieved using the differential capacitance sensing strategy. Referring to FIG. 30A, cavity stiffening can be represented by the attenuation of pressure sensitivity based on the stiffness $C_{cav}$, such as shown by equation (8):

$$H_{cavity} = \frac{C_{mep}}{C_{mep} + C_{cav}} \quad (8)$$

Therefore, the differential capacitance sensing strategy for the subject shear stress sensor can be highly effective in environments where the pressure forces in a turbulent flow can be approximately two orders of magnitude higher than the shear forces.

According to embodiments, the subject sensor can be used to measure in-plane deflections due to shear stress while minimizing out of plane deflections due to pressure. In addition, the mechanical structure, cavity, and vent design and the common mode rejection from the differential capacitive sensing scheme can help to mitigate transverse sensitivity.

Figure 30B:
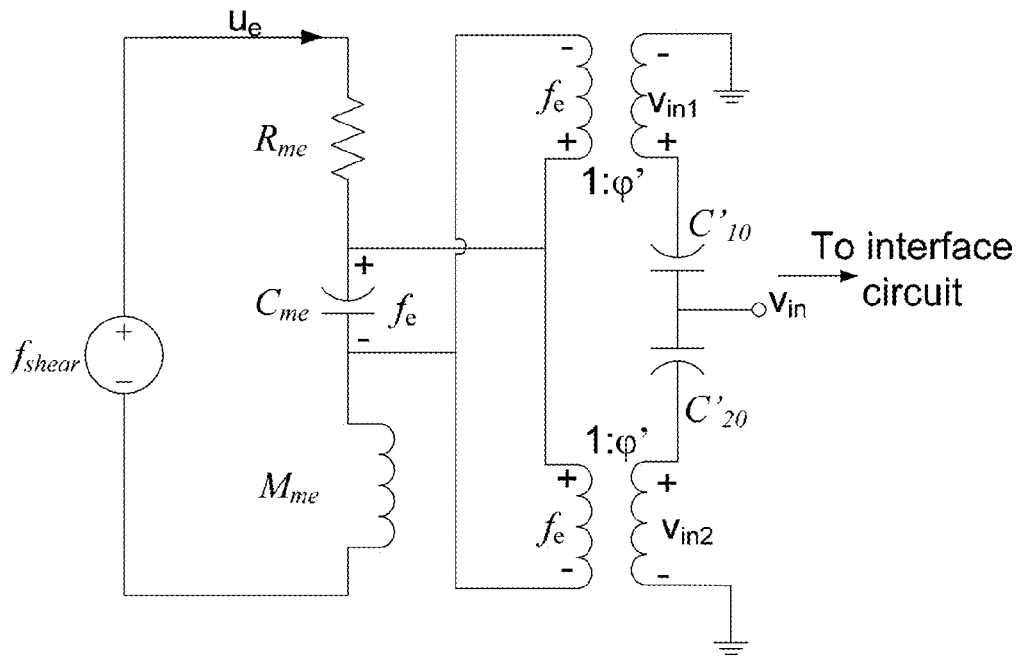

FIG. 30B shows a schematic of an equivalent circuit for a differential capacitive shear stress sensor according to an embodiment of the present invention. Here, the transduction from the mechanical deflection to electrical output can be modeled using a transformer, which is a two-port circuit element. Lumped element modeling (LEM) is used to represent energy storage and dissipation of the distributed mechanical system of the sensor structure using lumped elements such as lumped mass, compliance and resistance. The spatially distributed energy storage and dissipation are lumped about the central deflection. For this transducer, the lumped deflection is the floating element deflection given in equation (3). For estimating the system dynamic response, it is assumed that the system possesses weak electromechanical coupling, the amplifier has infinite (ideal) input impedance and an electronic bandwidth much higher than that of the sensor mechanical response. Thus the dynamic response of the sensor is dominated by the mechanical response of the sensor, which reduces to a simple second-order system.

Referring to FIG. 30B, the damping, $R_{me}$, arises predominantly from the complex flow through the various gaps and the flow underneath the sensor and is not modeled here for simplicity. Assuming an under-damped system, $R_{me}$ only affects the upper end of the bandwidth of the system mechanical response. The bandwidth of the sensor is thus proportional to the undamped mechanical resonant frequency $f_r$ given as equation (9):

$$f_r = \frac{1}{2\pi}\sqrt{\frac{1}{C_{me}M_{me}}}, \quad (9)$$

where $M_{me}$ and $C_{me}$ are lumped mechanical mass and compliance of the sensor, respectively. The lumped mass $M_{me}$ represents the storage of kinetic energy due to the motion of the structure. The compliance $C_{me}$ represents the storage of potential energy in the tether due to the deflection of the floating element.

Combining all the models together yields the static sensitivity of the sensor, given as equation (10):

$$S_{sensor} = V_B \frac{\delta/\tau_w}{g_{01}}. \quad (10)$$

Including the attenuation terms due to the asymmetric gap between comb fingers and the parasitic capacitance, the overall sensitivity of the sensor is given by equation (11):

$$S_{overall} = H_{gap}H_c S_{sensor}, \quad (11)$$

where $H_{gap}$ is the output voltage signal attenuation due to the asymmetric gap in the comb finger structure and $H_c$ is the attenuation due to $C_p$ and $C_i$ from the packaging and interface circuitry. The MDS or $\tau_{min}$ is defined as given in equation (12):

$$\tau_{min} = MDS = \frac{S_{output}|_{f=1\,kHz\,@1\,Hz\,bin}}{S_{overall}}. \quad (12)$$

where $S_{output}$ is the output voltage noise spectrum of the packaged sensor.

The optimization scheme is subjected to linearity, bandwidth constraints for a given maximum target shear stress. Additional modeling equations can be found in "Characterization of a MEMS-Based Floating Element Shear Stress Sensor" by Chandrasekharan et al. (AIAA 2009), which is hereby incorporated by reference in its entirety.

Table 1 provides the design geometry and the target specifications for a sensor in accordance with an example embodiment.

TABLE 1

Design specifications and optimal geometries.

| Specifications | Value | Optimum Geometries | Value |
| --- | --- | --- | --- |
| Target Shear Stress $\tau_{max}$ (Pa) | 5.0 | Tether Length $L_t$ (μm) | 1000 |
| Minimum Bandwidth $f_{min}$ (kHz) | 5.0 | Tether Width $W_t$ (μm) | 23 |
| Maximum Element Size $L_{e_{max}}$ (μm) | 2000 | Element Size $L_e$, $W_e$ (μm) | 2000 |
| Maximum Tether Length $L_{t_{max}}$ (μm) | 1000 | Tether/Element Thickness $T_t$ (μm) | 45 |
| Minimum Tether Width $W_{t_{min}}$ (μm) | 10 | Comb Finger Width $W_f$ (μm) | 5.0 |
| Minimum Element/Tether Thickness $T_{t_{min}}$ (μm) | 45 | Comb separation $g_{01}$ (μm) | 3.5 |
| Minimum Comb Finger Width $W_{f_{min}}$ (μm) | 4.0 | Comb finger length $L_f$ (μm) | 170 |
| Minimum Gap for Capacitors $[g_{01}, g_{02}]_{min}$ (μm) | 3.5 | Resonant Frequency $f_r$ (kHz) | 5.0 |

Figure 31:
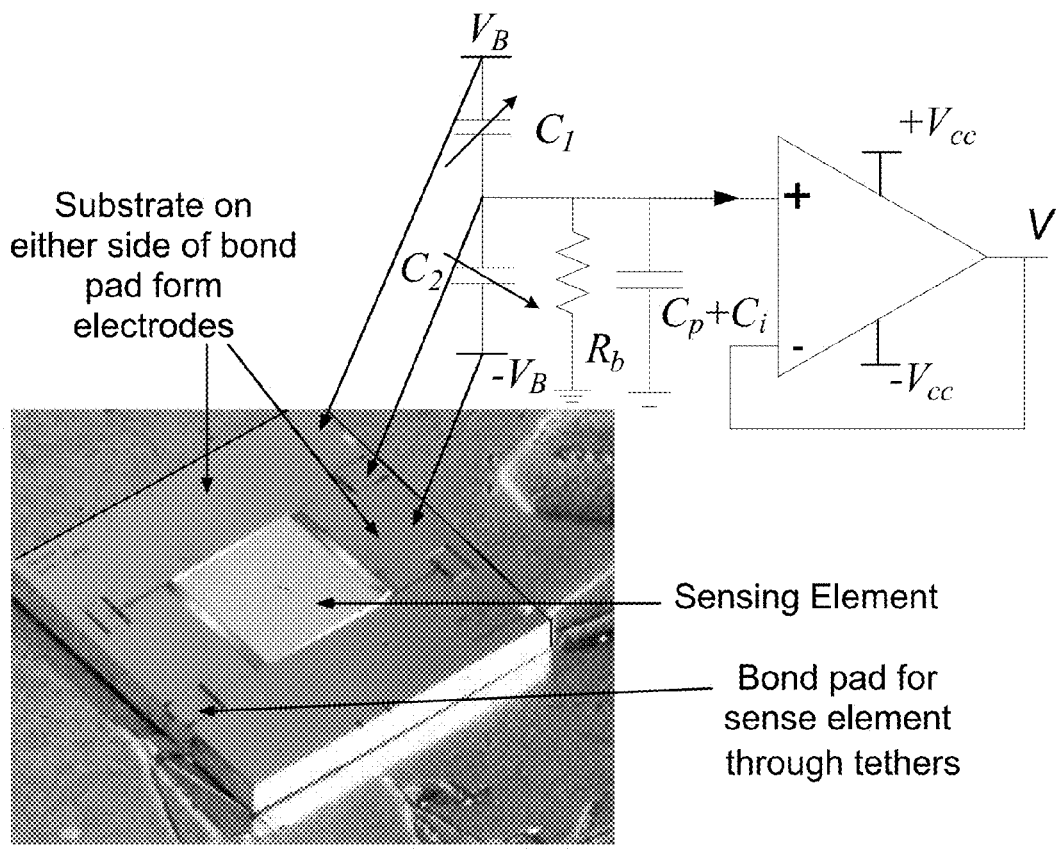
FIG. 31 shows a schematic and optical image of sensor die (5 mm×5 mm) indicating floating element, contact pads, and interface circuit (voltage buffer) in accordance with an embodiment of the present invention.

The example sensor was fabricated using silicon micromachining in accordance with an embodiment of the subject method of fabricating the sensor as described above with reference to FIGS. 3-9, resulting in a total die size of about 5 mm×5 mm. FIG. 31 shows an optical image of the fabricated sensor and a schematic of the interface circuit connections. The sensor is packaged in a printed circuit board (PCB) such that it is flush with the surface (see FIG. 32A). The amplifier (SiSonic™) is placed on the back side of the PCB in close proximity to the sensor (see FIG. 32B) to minimize parasitic attenuation arising from the connection traces on the PCB. The PCB is then mounted on to a Lucite plug for dynamic characterization in an acoustic plane wave tube (PWT) (see FIG. 33). The sensor was characterized for dynamic shear sensitivity, pressure sensitivity and frequency response in the PWT, while noise floor measurements were preformed in a Faraday cage.

Stokes layer excitation, from propagating acoustic plane waves was used to estimate the linearity and frequency response of the sensor. A known oscillating shear stress input was generated using acoustic plane waves in a duct. The oscillating acoustic field in conjunction with the no-slip boundary condition at the duct wall results in an oscillating velocity gradient, generating a frequency-dependent shear stress. This enables a theoretical estimate of the wall shear stress, if the acoustic pressure is known at a given axial location in the duct. The input shear stress, $\tau_{in}$, corresponding to the amplitude of the acoustic pressure, p' at a given frequency, $\omega$ is theoretically given as equation (13)

$$\tau_{in} = -\frac{p'\sqrt{j\omega v}}{c} e^{j(\omega t - kx_0)} \tanh\left(a\sqrt{\frac{j\omega}{v}}\right), \quad (13)$$

where V is the kinematic viscosity of air, c is the isentropic speed of sound or wave speed, k=$\omega$/c is the acoustic wave number and a is the duct width.

Figure 34:
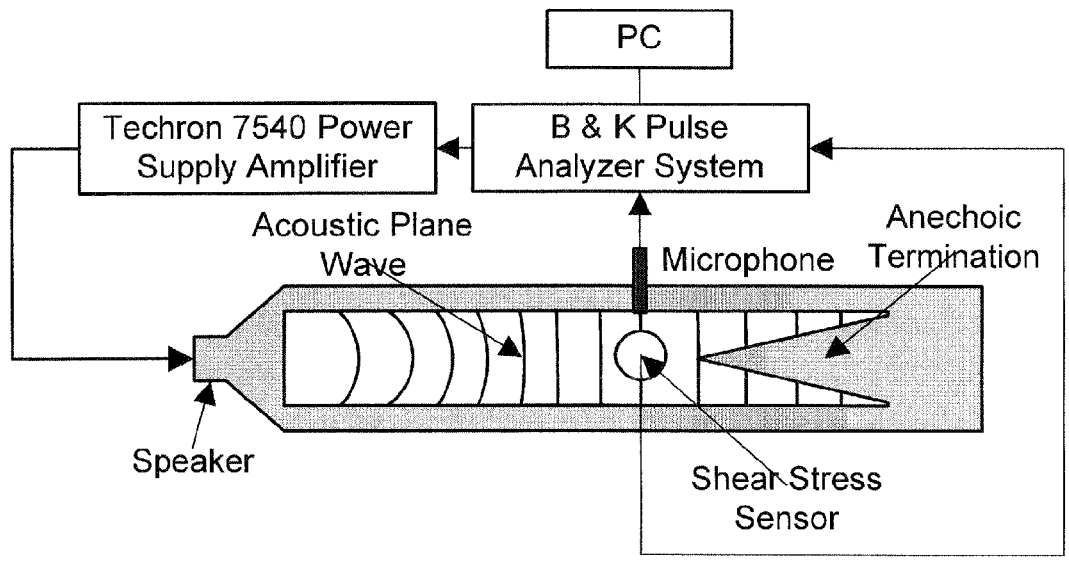
FIG. 34 shows a schematic of the dynamic calibration setup for shear stress measurement with plane progressive acoustic waves in accordance with an embodiment of the present invention.

FIG. 34 shows the schematic of the experimental setup for characterization. Plane waves generated by a BMS 4590P compression driver (speaker), mounted at one end of the PWT, propagate along the length of the tube fitted with an anechoic termination (a 30.7 long fiberglass wedge). The anechoic termination minimizes acoustic reflections to ensure plane propagating waves in the duct. The PWT consists of a square duct, 1"×1" in cross section, which has a cut-on of 6.7 kHz frequency for higher order acoustic modes. In this case, the expression in equation (13) is no longer valid in the presence of higher order modes beyond the cut-on frequency. The sensor being tested and a reference microphone (B&K 4138) are flush mounted at the same axial position along the length of the tube, which ensures they are subjected to the same acoustic signal. A B&K PULSE Multi-Analyzer System (Type 3109) acts as the microphone power supply, data acquisition unit, and signal generator for the compression driver.

Figure 35:
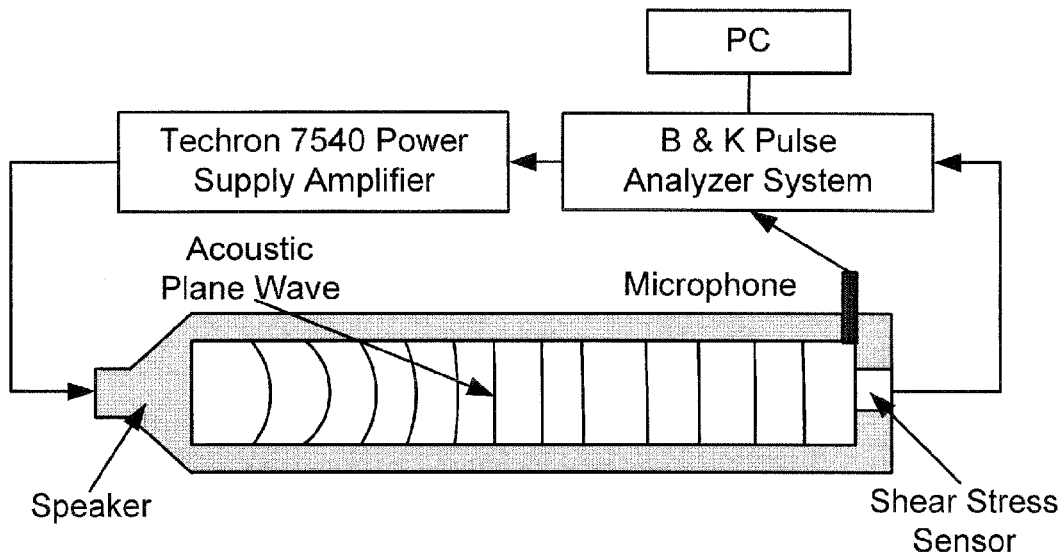
FIG. 35 shows a schematic of the dynamic calibration setup for measuring pressure sensitivity using normal incidence acoustic waves in accordance with an embodiment of the present invention.

In the test configuration described above, the shear stress sensor was subjected simultaneously to both transverse shear forces and normal forces (pressure). Thus, the sensor output voltage is the composite result of the multi-axis motion of the floating element if the sensor nominal capacitances are not matched (non-ideal case). To differentiate the shear stress sensitivity from the pressure sensitivity, the pressure response of the sensor was directly measured by mounting the sensor on a rigid plate at the end of the PWT (without the anechoic termination) to impart normal acoustic incidence (see FIG. 35).

The noise power spectral density of the sensor is measured in a double Faraday cage at different bias voltages. In this measurement, the output of the voltage follower is fed to the input of a SRS785 spectrum analyzer. The spectrum analyzer measures the output noise power spectral density (PSD) with a Hanning window to reduce spectral leakage effects. The noise measurement includes noise from the sensor and the interface electronics (amplifier). The setup noise from the spectrum analyzer was separately measured and subtracted from the sensor noise measurement.

Figure 36:
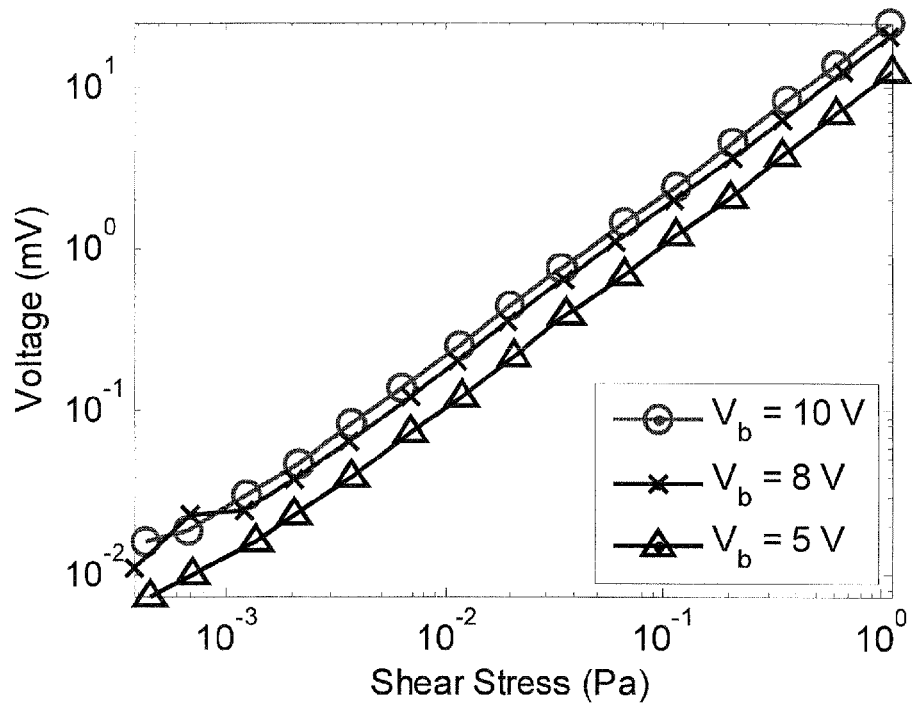
FIG. 36 shows a plot of linear sensor output voltage as a function of shear stress at 4.2 kHz at 3 different bias voltages: 5V, 8V, and 10V.
Figure 37:
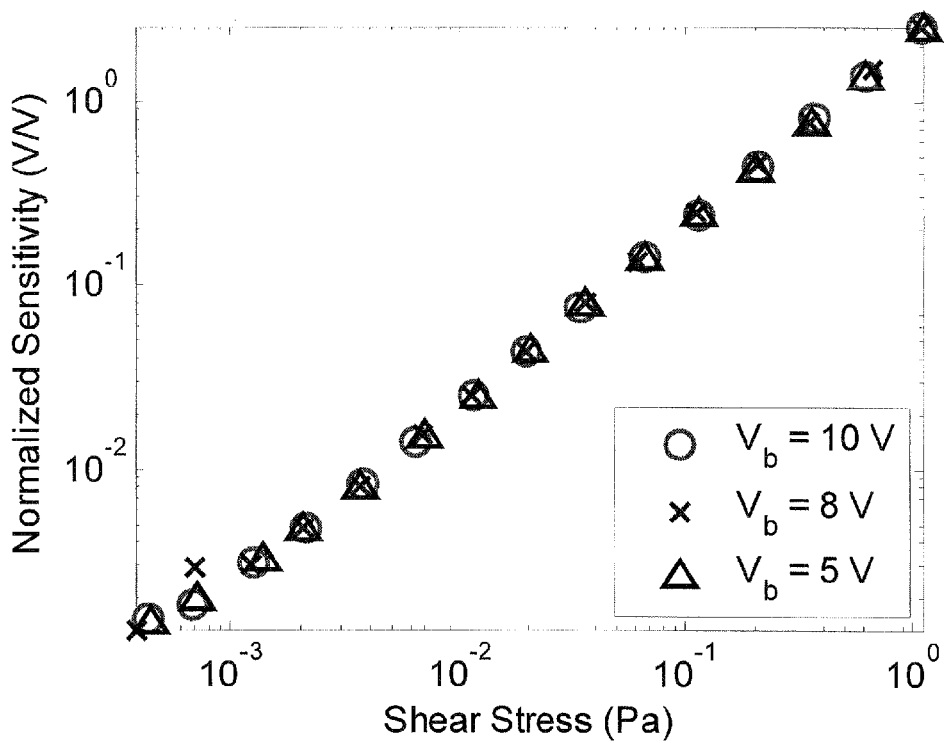
FIG. 37 shows a plot of sensor output voltage normalized by bias voltage as a function of shear stress at 4.2 kHz at 3 different bias voltages: 5V, 8V, and 10V.

The preliminary sensor characterization in the PWT involves three different measurements. The first measurement is of the sensor dynamic sensitivity measured at three different bias voltages, 5 V, 8 V, and 10 V, at a frequency of 4.2 kHz. This particular frequency was chosen to ensure sufficient shear stress even at low sound pressure level (SPL), which is limited by the driving capability of the compression driver (From equation (13), $\tau \sim p'\sqrt{\omega}$). The input shear stress is increased by raising the input sound pressure level (SPL) in steps of 5 dB from 80 dB to 150 dB. The upper and lower end of the SPL is set by the driving limit of the compression driver. The shear stress corresponding to the pressure input varies from 0.4 mPa to 1.16 Pa. The sensitivity plots corresponding to this measurement are shown in FIG. 36. The sensitivity of the sensor is deduced using a linear curve fit on the data set. In all three cases, the sensor exhibits a fairly linear sensitivity up to the testing limit of 1.1 Pa. From this data, the measured sensitivities are 23 mV/Pa, 19 mV/Pa, and 11 mV/Pa, respectively, at $V_B$=10 V, 8 V, and 5 V. The sensor sensitivity is directly proportional to the applied bias voltage as expected. This is further confirmed by the normalized sensitivity (output voltage divided by voltage bias) plot in FIG. 37. The normalized sensitivities show close agreement and are 2.268 mV/V/Pa, 2.316 mV/V/Pa and 2.196 mV/V/Pa, respectively, at $V_B$=10 V, 8 V, and 5 V. It should be noted that these measurements include voltage components due to pressure sensitivity of the sensor.

Figure 38:
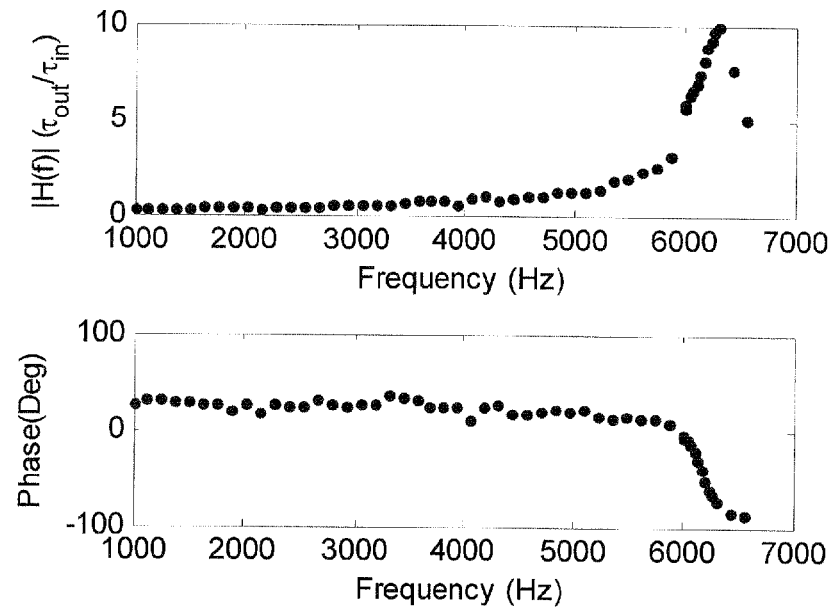
FIG. 38 shows a plot of frequency response of sensor at $V_B$=10 V using $\tau_{in}$=0.5 Pa as the reference signal up to the testing limit of 6.7 kHz (top plot shows magnitude, bottom plot shows phase).
Figure 39:
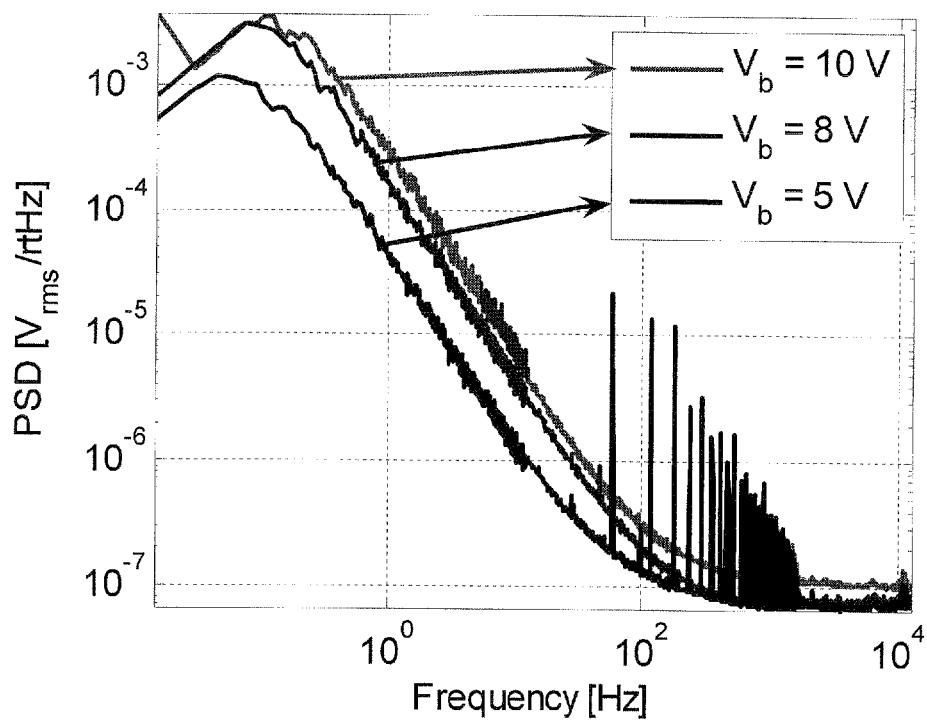
FIG. 39 shows a plot of measured output referred noise floor of the sensor of packaged sensor in $V_{rms}/\sqrt{Hz}$ at different bias voltages: 5V, 8V, and 10V.

The second measurement is of the frequency response of the sensor, which is measured at $V_B$=10 V. The expression of the frequency response normalized by the input shear stress is given by equation (14):

$$H(f) = \frac{V(f)}{\tau_{in}(f)} \frac{\partial \bar{\tau}}{\partial \bar{V}}, \quad (14)$$

where V(f) is the sensor output corresponding to the known shear stress input $\tau_{in}$, which is theoretically estimated using equation (13). The term $\partial\bar{\tau}/\partial\bar{V}$ is the inverse of the flat-band sensitivity of the sensor (for this measurement the sensitivity at 4.2 kHz is utilized). FIG. 38 shows the magnitude and phase of the measured frequency response function (FRF). As expected from the design, the FRF shows a clear second-order system response with a flat band region and a resonance frequency of 6.1 kHz. The non-zero phase difference between the measured signal and the theoretical input shear stress may be attributed to non-idealities such as contributions from the pressure response, weak reflections from the anechoic termination or phase shifts introduced by the interface electronics.

The third measurement is for the sensor noise floor measurements in the Faraday cage, which determine the lower end of the dynamic range of the sensor given by the MDS. The output noise spectral density at $V_B$=10 V is 114 nV/$\sqrt{Hz}$ at f=1 kHz with 1 Hz frequency bin. The MDS calculated from equation (12) using the sensitivity at $V_B$=10 V is 4.9 $\mu Pa|_{f=1\ kHz@1\ Hz\ bin}$. This translates into a dynamic range>106 dB, considering that the upper shear stress of the test setup was limited to 1.1 Pa and the output was still linear (see FIG. 36). The sensor was designed for $\tau_{max}$=5 Pa and demonstrated linearity up to 1.1 Pa, indicating that it potentially possesses a dynamic range higher than the measured value. If the lull 5 Pa upper shear stress design limit were achieved, the device would possess a dynamic range of 120 dB.

Figure 40:
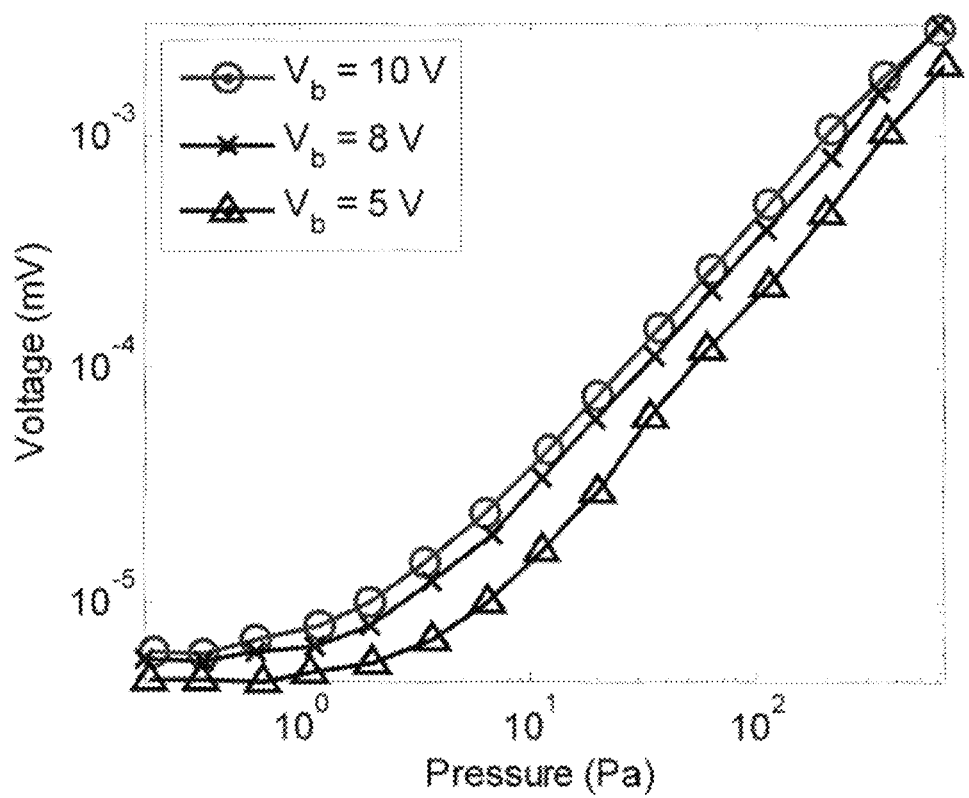
FIG. 40 shows a plot of voltage output as a function of pressure at 4.2 kHz at different bias voltages: 5V, 8V, and 10V.

The sensor mounted at the end of the PWT for normal acoustic incidence is also experimentally characterized for pressure sensitivity at 4.2 kHz (see FIG. 40). The SPL range for the experiment was 80 dB-150 dB in steps of 5 dB, identical to that used for the shear sensitivity tests. The pressure sensitivity of the sensor at $V_B$=10 V is 4.8 µV/Pa, which is about 1000 times smaller than the composite shear and pressure sensitivity of the sensor (see FIG. 36 and FIG. 40). A comparison of these sensitivities at $V_B$=10 V result in a pressure rejection, $H_p$, of approximately 74 dB, which is computed as equation (15)

$$H_p = 20 \log(S_{shear}/S_{pressure}). \quad (15)$$

As presented above, the example sensor demonstrated a linear response up to the testing limit of 1.1 Pa and a flat frequency response with resonance at 6.1 kHz. In addition, the sensor demonstrated a dynamic range 1.1 Pa-4.9 µPa, or 106 dB. The pressure rejection achieved via structural design and interface electronics is approximately 74 dB.

Accordingly, embodiments of the subject sensor can be effective for shear stress measurements in many applications.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A microscale sensor for direct shear stress measurement, comprising:
   a floating element, wherein the floating element comprises a first set of capacitive comb fingers extending from a first side of the floating element;
   at least one tether extending from the floating element for anchoring the floating element to a stationary surface; and
   a first set of stationary capacitive comb fingers interdigitated with the first set of capacitive comb fingers of the floating element such that initial gaps between fingers of the interdigitated first set of stationary capacitive comb fingers and first set of capacitive comb fingers are non-uniform.

2. The microscale sensor according to claim 1, further comprising a second set of capacitive comb fingers extending from a second side of the floating element; and
   and a second set of stationary capacitive comb fingers interdigitated with the second set of capacitive comb fingers of the floating element such that initial gaps between fingers of the interdigitated second set of stationary capacitive comb fingers and second set of capacitive comb fingers are non-uniform.

3. The microscale sensor according to claim 2, wherein the first set of stationary capacitive comb fingers interdigitated with the first set of capacitive comb fingers of the floating element is configured for connection to a first voltage; and
   wherein the second set of stationary capacitive comb fingers interdigitated with the second set of capacitive comb fingers of the floating element is configured for connection to a second voltage, wherein the second voltage has opposite polarity to the first voltage.

4. The microscale sensor according to claim 3, further comprising:
   a voltage read-out circuit connected to the floating element.

5. The microscale sensor according to claim 4, wherein the voltage read-out circuit comprises a voltage buffer amplifier.

6. The microscale sensor according to claim 2, wherein the at least one tether comprises:
   a first tether and a second tether extending from the first side of the floating element with the first set of stationary capacitive comb fingers disposed therebetween; and
   a third tether and a fourth tether extending from the second side of the floating element with the second set of stationary capacitive comb fingers disposed therebetween.

7. The microscale sensor according to claim 1, wherein capacitance is provided between a non-fingered side of the floating element and a side of a stationary substrate that is adjacent the non-fingered side of the floating element.

8. The microscale sensor according to claim 1, wherein capacitance is provided between the at least one tether comprising the conductive material and a side of a stationary substrate that is adjacent the at least one tether.

9. The microscale sensor according to claim 8, wherein the at least one tether comprises a first tether and a second tether extending from the first side of the floating element with the first set of stationary capacitive comb fingers disposed therebetween, the first tether being non-uniformly spaced apart from the side of the stationary substrate adjacent the first tether and the second tether being uniformly spaced apart from the side of the stationary substrate adjacent the second tether.

10. The microscale sensor according to claim 9, wherein the at least one tether further comprises a third tether and a fourth tether extending from a second side of the floating element, the third tether being uniformly spaced apart from the side of the stationary substrate adjacent the third tether and the fourth tether being non-uniformly spaced apart from the side of the stationary substrate adjacent the fourth tether, wherein the third tether is disposed symmetric to the first tether and the fourth tether is disposed symmetric to the second tether.

11. The microscale sensor according to claim 10, wherein the non-uniform spacing of the first tether is rotationally symmetric to the non-uniform spacing of the fourth tether and the uniform spacing of the second tether is rotationally symmetric to the uniform spacing of the third tether.

12. The microscale sensor according to claim 1, further comprising a protective coating on the floating element, the at least one tether, and the first set of stationary capacitive comb fingers.

13. The microscale sensor according to claim 1, further comprising a cavity below the floating element, wherein the cavity comprises a vent configured for exposure to an ambient.

14. The microscale sensor according to claim 13, wherein the cavity and the vent are sized so as to maximize the RC time constant pressure sensitivity cut-on.

15. The microscale sensor according to claim 14, wherein gaps between the floating element, sides of a stationary substrate, the at least one tether, and the first set of stationary capacitive comb fingers provide the vent for the cavity.

16. The microscale sensor according to claim 14, wherein the vent is disposed at a lateral side of the cavity.

17. The microscale sensor according to claim 14, wherein the vent is disposed at a top side of the cavity.

18. A microscale sensor comprising:
   a floating element;
   at least one tether extending from the floating element for anchoring the floating element to a stationary surface;
   a comb drive comprising fingers disposed orthogonal to displacement of the floating element, the comb drive being asymmetric for variable gap transduction; and
   a cavity disposed below the floating element, the cavity vented for exposure to an ambient.

19. The microscale sensor according to claim 18, wherein the at least one tether is disposed orthogonal to displacement of the floating element.

20. The microscale sensor according to claim 19, wherein the at least one tether comprises four tethers, the four tethers being spaced apart from the stationary surface for variable gap transduction.

21. The microscale sensor according to claim 18, wherein the floating element and the at least one tether are configured to result in additional capacitance change when measuring shear stress.

22. The microscale sensor according to claim 21, further comprising a protective dielectric coating on the floating element and comb drive.

23. The microscale sensor according to claim 22, wherein the cavity is vented through a side of the microscale sensor or from the top.

24. The microscale sensor according to claim 18, wherein the floating element, the at least one tether, the comb drive, and the cavity are all formed from a single material layer.

25. A method for fabricating a microscale flow-rate/skin friction sensor, comprising:
   performing a first mask process on a front side of a substrate to form a first mask defining sensor features;
   etching the front side of the substrate using the first mask to form sensor features;
   forming a conductive material on the sensor features;
   performing a second mask process on a back side of the substrate to form a second mask defining a backside cavity after forming the conductive material; and
   etching the back side of the substrate using the second mask to form the backside cavity.

26. A method for fabricating a microscale flow-rate/skin friction sensor, comprising:
   performing a first mask process on a front side of a substrate to form a first mask defining all sensor structures; and
   etching the front side of the substrate using the first mask as an etch mask to form the sensor structures.

* * * * *

UNITED STATES PATENT AND TRADEMARK OFFICE
CERTIFICATE OF CORRECTION

PATENT NO. : 8,833,175 B2
APPLICATION NO. : 13/133303
DATED : September 16, 2014
INVENTOR(S) : Vijay Chandrasekharan et al.

It is certified that error appears in the above-identified patent and that said Letters Patent is hereby corrected as shown below:

In the Specification

Column 4,
Line 18, "shear three causes" should read --shear force causes--.

Column 5,
Line 32, "a SOT wafer" should read --a SOI wafer--.

Column 5,
Line 40, "the SOT wafer" should read --the SOI wafer--.

Column 5,
Line 56, "SOT substrates." should read --SOI substrates.--.

Column 6,
Line 36, "a DRIB." should read --a DRIE.--.

Column 6,
Lines 40-41, "HF in a specific" should read --HF. In a specific--.

Column 10,
Line 25, "< $g_{02}$)." should read --< $g_{02}$.--.

Column 13,
Line 38, "and a is the" should read --and α is the--.

Column 13,
Line 43, "(a 30.7 long" should read --(a 30.7" long--.

Signed and Sealed this
Seventh Day of April, 2015

Michelle K. Lee
*Director of the United States Patent and Trademark Office*

Column 15,
Line 5, "the lull 5" should read --the full 5--.